(12) United States Patent
Henry et al.

(10) Patent No.: US 9,005,548 B2
(45) Date of Patent: Apr. 14, 2015

(54) METHODS FOR FABRICATING HIGH ASPECT RATIO PROBES AND DEFORMING HIGH ASPECT RATIO NANOPILLARS AND MICROPILLARS

(75) Inventors: Michael D. Henry, Altadena, CA (US); Andrew P. Homyk, South Pasadena, CA (US); Axel Scherer, Laguna Beach, CA (US); Thomas A. Tombrello, Altadena, CA (US); Sameer Walavalkar, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 481 days.

(21) Appl. No.: 12/712,097

(22) Filed: Feb. 24, 2010

(65) Prior Publication Data

US 2010/0215543 A1 Aug. 26, 2010

Related U.S. Application Data

(60) Provisional application No. 61/208,528, filed on Feb. 25, 2009, provisional application No. 61/164,289, filed on Mar. 27, 2009, provisional application No. 61/220,980, filed on Jun. 26, 2009.

(51) Int. Cl.
| | | |
|---|---|---|
| *B01L 3/00* | (2006.01) | |
| *H01L 21/308* | (2006.01) | |
| *B81C 1/00* | (2006.01) | |
| *H01L 21/3065* | (2006.01) | |

(52) U.S. Cl.
CPC ........ *H01L 21/3086* (2013.01); *B81C 1/00111* (2013.01); *H01L 21/3065* (2013.01); *H01L 21/3081* (2013.01); *B81B 2203/0361* (2013.01); *B81B 2207/056* (2013.01); *H01L 21/30655* (2013.01)

(58) Field of Classification Search
CPC .................................................. B81C 1/00071
USPC .................. 216/13, 40, 41; 977/701; 422/551
See application file for complete search history.

(56) References Cited

U.S. PATENT DOCUMENTS

| 4,322,571 | A | 3/1982 | Stanbery |
| 6,586,787 | B1 | 7/2003 | Shih et al. |
| 6,593,065 | B2 | 7/2003 | Scherer |
| 6,831,017 | B1 | 12/2004 | Li et al. |
| 7,019,325 | B2 | 3/2006 | Li et al. |
| 7,302,146 | B2 | 11/2007 | Turner et al. |
| 7,387,967 | B2 | 6/2008 | Ogawa et al. |
| 7,419,908 | B2 | 9/2008 | Green |
| 7,906,803 | B2 | 3/2011 | Shioya et al. |
| 7,947,430 | B2 | 5/2011 | Fu et al. |
| 7,998,788 | B2 | 8/2011 | Guha et al. |
| 8,067,763 | B2 | 11/2011 | Wang et al. |
| 8,080,468 | B2 | 12/2011 | Scherer et al. |
| 8,114,774 | B2 | 2/2012 | Hurkx et al. |
| 8,154,093 | B2 | 4/2012 | Bradley et al. |
| 8,183,587 | B2 | 5/2012 | Samuelson et al. |
| 8,198,706 | B2 | 6/2012 | Kamins et al. |
| 2002/0127495 | A1* | 9/2002 | Scherer ......................... 430/314 |
| 2004/0071951 | A1 | 4/2004 | Jin |
| 2004/0108298 | A1 | 6/2004 | Gao |
| 2006/0063368 | A1 | 3/2006 | Sharma |
| 2006/0088995 | A1* | 4/2006 | Zhang et al. .................. 438/627 |
| 2006/0118975 | A1 | 6/2006 | Koenenkamp |
| 2006/0131695 | A1 | 6/2006 | Kuekes et al. |
| 2006/0207647 | A1 | 9/2006 | Tsakalakos et al. |
| 2007/0126079 | A1 | 6/2007 | Shioya et al. |
| 2007/0132043 | A1 | 6/2007 | Bradley et al. |
| 2008/0009121 | A1 | 1/2008 | Wei |
| 2008/0035983 | A1 | 2/2008 | Sandhu et al. |
| 2008/0036038 | A1 | 2/2008 | Hersee et al. |
| 2008/0092938 | A1 | 4/2008 | Majumdar et al. |
| 2008/0102319 | A1 | 5/2008 | Bratkovski et al. |
| 2008/0142970 | A1 | 6/2008 | Evans et al. |
| 2008/0149944 | A1 | 6/2008 | Samuelson et al. |
| 2008/0156369 | A1 | 7/2008 | Ko et al. |
| 2008/0203431 | A1 | 8/2008 | Garcia et al. |
| 2008/0211040 | A1 | 9/2008 | Lieber et al. |
| 2008/0230802 | A1 | 9/2008 | Bakkers et al. |
| 2010/0006817 | A1 | 1/2010 | Ohlsson et al. |
| 2010/0033561 | A1 | 2/2010 | Hersee |
| 2010/0068828 | A1 | 3/2010 | Thomas |
| 2010/0176822 | A1 | 7/2010 | Offermans et al. |
| 2010/0213579 | A1 | 8/2010 | Henry et al. |
| 2010/0215543 | A1 | 8/2010 | Henry et al. |
| 2010/0291385 | A1 | 11/2010 | Greer et al. |
| 2011/0020960 | A1 | 1/2011 | Henry et al. |
| 2011/0031470 | A1 | 2/2011 | Scherer et al. |

FOREIGN PATENT DOCUMENTS

| JP | H06-045613 | 2/1994 |
| JP | 2006332662 | 1/2006 |

(Continued)

OTHER PUBLICATIONS

Timoshenko, S., Analysis of Bi-metal Thermostats, Journal of the Optical Society of America 1925, 11: 1235-1257.

(Continued)

*Primary Examiner* — Natalia Levkovich
(74) *Attorney, Agent, or Firm* — Steinfl & Bruno, LLP

(57) ABSTRACT

Methods for fabricating of high aspect ratio probes and deforming micropillars and nanopillars are described. Use of polymers in deforming nanopillars and micropillars is also described.

3 Claims, 22 Drawing Sheets

(56) References Cited

FOREIGN PATENT DOCUMENTS

| JP | 2006-505119 | 2/2006 |
|---|---|---|
| JP | 2004-193525 | 8/2007 |
| JP | 2007-194646 | 8/2007 |
| JP | 2008/130712 | 6/2008 |
| JP | 2008130712 | 6/2008 |
| JP | 2010535406 | 11/2010 |
| WO | 2007077842 | 7/2007 |
| WO | 2009017604 | 2/2009 |
| WO | 2010/099216 | 9/2010 |
| WO | 2010/099220 | 9/2010 |
| WO | 2010/151604 | 12/2010 |

OTHER PUBLICATIONS

Nassiopoulos, A., et al., Electroluminescent Device Based on Silicon Nanopillars, Applied Physics Letters 1996, 69: 2267-2269.
Zailer, I., et al., Crosslinked PMMA as a High-resolution Negative Resist for Elctron Beam Lithography and Applications for Physics of lowdimensional Structures, Seminconductor Sci. Technol. 1996, 11: 1235-1238.
Photopoulos, P., et al. Photoluminescence from Nanocrystalline Silicon in Si/SiO2 Superlattices, Applied Physics Letters 2000, 76: 3588-3590.
Bogglid, P., et al., Fabrication and Actuation of Customized Nanotweezers with a 25 nm Gap, Nanotechnology 2001, 12: 331-335.
Lauhon, L., et al., Epitaxial Core-shell and Core-multishell Nanowire Heterostructures, Nature 2002, 420: 57-61.
de Boer, M., et al., Guidelines for Etching Silicon MEMS Structures Using Flourine High-density Plasmas at Cryogenic Temperatures, Journal of Microelectromechanical Systems 2002, 11: 385-401.
Rangelow, I.W., et al., Critical Tasks in High Aspect Ratio Silicon Dry Etching for Microelectromechanical Systems, Journal of Vaccum Science Technology A 2003, 21: 1150-1562.
Williams, K.R., et al., Etch Rates for Micromachining Processing Part, Journal of Microelectromechanical Systems 2003, 12: 761-778.
Singh, J., Electronic and Optoelectronic Properties of Semiconductor Structures, In Electronic and Optoelectronic Properties of Semiconductor Structures, 2003, Cambridge University Press, Chapter 1.4 Strained heterostructures, 26-31.
Teh, W., et al., Cross-linked PMMA as a low Dimensional Sacrificial Layer, Journal of Electromechanical Systems 2003, 12: 641-648.
Scheible, D., et al., Silicon Nanopillars for Mechanical Single-electron Transport, Applied Physics Letters 2004, 84: 4632-4634.
Kayes, B.M., et al., Comparison of the Device Physics Principles of p—n Junction Nanorod Solar Cells, Journal of Applied Physics 2005, 97: 114302-1 114302-11.
Yeom, J., et al., Maximum Achievable Aspect Ratio in Deep Reactive Ion Etching of Silicon due to Aspect Ratio Dependent Transport and the Microloading Effect, Journal of Vacuum Science Technology 2005, 23: 2319-2329.
Tang, Z., et al., Physical models for coupled electromechanical analysis of silicon nanoelectromechanical systems, Journal of Applied Physics 2005, 97: 114304-1 114304-13.
Tang, Z., et al., Finite Temperature Quasicontinuum Method for Multiscale Analysis of Silicon Nanostructures, Physical Review 2006, 74: 064100-1 061400-29.
Singh, N., et al., High-Performance Fully Depleted Silicon Nanowire (Diameter ≤ 5 nm) Gate-All-Around CMOS Devices, IEEE Electron Device Letters 2006, 27:383-386.
Welch, C.C., et al., Silicon Etch Process Options for Micro-and Nanotechnology Using Inductively Coupled Plasmas, Microelectronic Engineering 2006, 83: 1170-1173.
Jacobsen, R., et al., Strained Silicon as a New Electro-optic Material, Nature 2006, 441: 199-202.
Sainiemi, L., et al., Rapid Fabrication of High Aspect Ratio Silicon Nanopillars for Chemical Analysis, Nanotechnology 2007, 18: 505303-1 505303-7.

Chang, Y.F., et al., Fabrication of High-aspect-ratio Silicon Nanopillar Arrays with the Conventional Reactive Ion Etching Technique, Applied Physics A 2007, 86: 193-196.
Sainiemi, L., et al., Mask Material Effects in Cryogenic Deep Reactive Ion Etching, Journal of Vacuum Science Technology B 2007, 25: 801-807.
Kim, H., et al., Field Emission From a Single Nanomechanical Pillar, Nanotechnology 2007, 18: 065201-1 065201-4.
Hashemi, P., et al., Asymmetric Strain in Nanoscale Patterned Strained-Si/strained-Ge/strained-Si Heterostructures on Insulator, Applied Physics Letters 2007, 91: 083109-1 083109-3.
Moser, B., et al., Strength and Fracture of Si Micropillars: A new scanning electron microscopy-based micro-compression test, Journal of Material Resources 2007, 22: 1004-1011.
Chen, M., et al., Self-masked High-aspect-ratio Polymer Nanopillars, Nanotechnology 2008, 19: 505301-1 505301-7.
Kelzenberg, M.D., et al., Single-nanowire Si Solar Cells, Nanotechnology Letters 2008, 8: 710-714.
Hon, K., et al., Periodically Poled Silicon, Applied Physics Letters 2009, 94: 091116-1 091116-3.
Sajjad, R., et al., Electronic Properties of a Strained <100> Silicon Nanowire, Journal of Applied Physics 2009, 105: 044307-1 044307-6.
Ambrose, D. et al. Vapour pressures up to their critical temperatures of normal alkances and 1-alkanols, *Pure & Appl. Chem.*, 1989, vol. 61, No. 8, pp. 1395-1403.
Barrett, C.S. et al. Lattice Constants of Gallium at 297 K, Nature 1965, vol. 207, p. 1382.
Cassie, A.B.D. et al. Wettability of Porous Surfaces, Transactions of the Faraday Society, 1944, vol. 40, pp. 546-551.
Chekurov, N., et al., The Fabrication of Silicon Nanostructures by Local Gallium Implantation and Cryogenic Deep Reactive Ion Etching, Nanotechnology 2009, 20: 065307-1-065307-5.
Chirico, R.D. et al. Vapor Pressure of on-Alkanes Revisited. New High-Precision Vapor pressure Data on n-Decane, n-Eicosane, and n-Octacosane, *J. Chem. Eng. Data*, 1989, vol. 34, pp. 149-156.
Ebron, V.H. et al. Fuel-Powered Artificial Muscles, *Science*, Mar. 17, 2006, vol. 311, pp. 1580-1583.
Frey, L., et al., Nanoscale Effects in Focused Ion Beam Processing, Applied Physics A: Materials Science & Processing 2003, 76: 1017-1023.
Gao, L. et al. The "Lotus Effect" Explained: Two Reasons Why Two Length Scales of Topography Are Important, *Langmuir*, 2006, vol. 22, pp. 2966-2967.
Gates, B., et al., New Approaches to Nanofabrication: Molding, Printing, and Other Techniques, Chemical Reviews 2005, 105: 1171-1196.
Gierak, J., et al., Exploration of the Ultimate Patterning Potential Achievable with High Resolution Focused Ion Beams, Applied Physics A: Materials Science & Processing 2005, 80: 187-194.
Henry, M.D. et al. Alumina etch masks for fabrication of high-aspect-ratio silicon micropillars and nanopillars, *Nanotechnology*, 2009, vol. 20, 255305 (pp. 1-4).
Kato, N.I., et al., Side-wall Damage in a Transmission Electron Microscopy Specimen of Crystalline Si Prepared by Focused Ion Beam Etching, Journal of Vacuum Science Technology A 1999, 17: 1201-1204.
Kuan W.-F. et al. The Preparation of superhydrophobic surfaces of hierarchical silicon nanowire structures, *Nanotechnology*, 2009, vol. 20, 035605 (pp. 1-8).
Jansen, H.V., et al., Black Silicon Method X: A Review on High Speed and Selective Plasma Etching of Silicon with Profile Control: An In-Depth Comparison Between Bosch and Cryostat DRIE Processes as a Roadmap to Next Generation Equipment, Journal of Micromechanics and Microengineering 2009, 19: 033001-1-033001-41.
Li, H. et al. Investigation of capacitive humidity sensing behavior of silicon nanowires, *Physica E.*, 2009, vol. 41, pp. 600-604.
Marrian, C., et al., Nanofabrication, Journal of Vacuum Science Technology A 2003, 21: S207-S215.
Melngailis, J., et al., A Review of Ion Projection Lithography, Journal of Vacuum Science Technology B 1998, 16: 927-957.

(56) References Cited

OTHER PUBLICATIONS

Mosher, L., et al., Double-Exposure Grayscale Photolithography, Journal of Microelectromechanical Systems 2009, 18: 308-315.

Qian, H.X., et al., Fabrication of Si Microstructures Using Focused Ion Beam Implantation and Reactive Ion Etching, Journal of Micromechanics and Microengineering 2008, 18: 035003-1-035003-5.

Schmidt, B., et al., Etch Rate Retardation of $Ga^+$-Ion Beam-Irradiated Silicon, Journal of the Electrochemical Society 2005, 152: G875-G879.

Schmidt, B., et al., Writing FIB Implantation and Subsequent Anisotropic Wet Chemical Etching for Fabrication of 3D Structures in Silicon, Sensors and Actuators A: Physical 1997, 61: 369-373.

Sunkara, M.K., et al., Bulk Synthesis of Silicon Nanowires Using a Low-Temperature Vapor-Liquid-Solid Method, Applied Physics Letters 2001, 79: 1546-1548.

Tseng, A., Recent Developments in Micromilling Using Focused Ion Beam Technology, Journal of Micromechanics and Microengineering 2004, 14: R15-R34.

Tseng, A., Recent Developments in Nanofabrication Using Ion Projection Lithography, Small 2005, 1: 594-608.

Tseng, A., Milling of Submicron Channels on Gold Layer Using Double Charged Arsenic Ion Beam, Journal of Vacuum Science & Technology B: Microelectronics and Nanostructures 2004, 22: 82-89.

Watt, F., et al., Ion Beam Lithography and Nanofabrication: A Review, International Journal of Nanoscience 2005, 4: 269-286.

Wiener, H. Vapor Pressure-Temperature Relationships Among the Branched Paraffin Hydrocarbons, ACS, 1948, pp. 425-430.

Zhou, Z., et al., Two-Beam-Current Method for E-Beam Writing Gray-Scale Masks and Its Application to High-Resolution Microstructures, Applied Optics 2008, 47: 3177-3184.

Oxford Plasma Technology Applications Engineering Group "Plasmalab" Process Data Sheet, 'Bosch' Silicon Etch Process, 'Cryo' Silicon Etch Process, and Silicon Etch Process.

European Communication Pursuant to Rules 70(2) and 70a(2) EPC dated Jun. 20, 2014 for EP Application No. 10792619.8 filed on Jun. 23, 2010 in the name of California Institute of Technology.

Japanese Office Action mailed on Aug. 19, 2014 for JP Application No. 2012-517704 filed on Feb. 4, 2010 in the name of California Institute of Technology—Japanese with English Translation.

Restriction Requirement mailed on Mar. 30, 2011 for U.S. Appl. No. 12/822,109, filed Jun. 23, 2010 in the name of California Institute of Technology.

Notice of Allowance mailed on Sep. 12, 2011 for U.S. Appl. No. 12/822,109, filed Jun. 23, 2010 in the name of California Institute of Technology.

Non-Final Office Action mailed on May 7, 2013 for U.S. Appl. No. 13/286,008, filed Dec. 31, 2011 in the name of California Institute of Technology.

Notice of Allowance mailed on Aug. 12, 2013 for U.S. Appl. No. 13/286,008, filed Dec. 31, 2011 in the name of California Institute of Technology.

Restriction Requirement mailed on Aug. 29, 2012 for U.S. Appl. No. 12/949,758, filed Nov. 18, 2010 in the name of California Institute of Technology.

Non-Final Office Action mailed on Sep. 19, 2012 for U.S. Appl. No. 12/949,758, filed Nov. 18, 2010 in the name of California Institute of Technology.

Final Office Action mailed on Mar. 4, 2013 for U.S. Appl. No. 12/949,758, filed Nov. 18, 2010 in the name of California Institute of Technology.

Non-Final Office Action mailed on Jun. 19, 2013 for U.S. Appl. No. 12/949,758, filed Nov. 18, 2010 in the name of California Institute of Technology.

Final Office Action mailed on Oct. 17, 2013 for U.S. Appl. No. 12/949,758, filed Nov. 18, 2010 in the name of California Institute of Technology.

Notice of Allowance mailed on May 20, 2014 for U.S. Appl. No. 12/949,758, filed Nov. 18, 2010 in the name of California Institute of Technology.

Non-Final Office Action mailed on Oct. 24, 2012 for U.S. Appl. No. 12/952,181, filed Nov. 22, 2010 in the name of California Institute of Technology.

Final Office Action mailed on Mar. 19, 2013 for U.S. Appl. No. 12/952,181, filed Nov. 22, 2010 in the name of California Institute of Technology.

Non-Final Office Action mailed on Jul. 23, 2013 for U.S. Appl. No. 12/952,181, filed Nov. 22, 2010 in the name of California Institute of Technology.

Final Office Action mailed on Apr. 7, 2014 for U.S. Appl. No. 12/952,181, filed Nov. 22, 2010 in the name of California Institute of Technology.

Advisory Action mailed on Jun. 25, 2014 for U.S. Appl. No. 12/952,181, filed Nov. 22, 2010 in the name of California Institute of Technology.

\* cited by examiner

METHODS FOR FABRICATING HIGH ASPECT RATIO PROBES AND DEFORMING HIGH ASPECT RATIO NANOPILLARS AND MICROPILLARS

CROSS REFERENCE TO RELATED APPLICATIONS

The present application claims priority to U.S. Prov. App. No. 61/208,528 filed on Feb. 25, 2009, and U.S. Prov. App. No. 61/164,289 filed on Mar. 27, 2009, both of which are incorporated herein by reference in their entirety. The present application also claims priority to U.S. Application No. 61/220,980 filed Jun. 26, 2009. The present application is also related to U.S. patent application Ser. No. 12/711,992 for 'Methods for fabricating high aspect ratio micropillars and nanopillars' filed on Feb. 24, 2010, the disclosure of which is also incorporated herein by reference in its entirety.

STATEMENT OF GOVERNMENT GRANT

The U.S. Government has certain rights in this invention pursuant to Grant No. DMR0520565 awarded by the National Science Foundation.

FIELD

The present disclosure relates to probes, micropillars and nanopillars. More in particular, the present disclosure relates to methods for fabricating high aspect ratio probes and deforming high aspect ratio micropillars and nanopillars.

BACKGROUND

Defining high aspect ratio structures with controllable sidewalls in silicon has become increasingly important both in the nanometer and micrometer scale for solar cells, microelectronic devices, and chemical analysis (see, for example, references 1-5). High aspect ratio micrometer pillars are used for solar cell investigations while nanometer scale high aspect ratio pillars are enabling fundamental investigations in theories of nanopillar stress mechanics (see, for example, reference 5), silicon based lasers, and nanoelectronic devices such as finFETs (see, for example, reference 2). Currently various nanofabrication techniques exist that rely on self assembly or bottom-up processing (see, for example, reference 6). Some top-down processing enabling reproducibility in nanofabrication can be found, for example, in references 7-8.

Further applications are high surface area chemical sensors (see, for example, reference 3) mechanical oscillators (see, for example, references 15-16) and piezo-resistive sensors. High aspect ratio pillars with diameters between 50-100 nm could prove useful for core-shell type plasmonic resonators (see, for example, reference 17) while pillars with sub-10 nm diameters have shown promising light emission characteristics (see, for example, references 18-19).

When fabricating high aspect ratio nanopillars and micropillars, smooth sidewalls with controllable angles, and precision patterning is highly desirable. Moreover, high reproducibility and cost reduction involves reliable reproduction of identical structures and critical positioning of such structures (see, for example, references 20-21, for experimental applications). Achieving these criteria has been greatly enhanced by inductively coupled plasma (ICP) etching techniques. Etches utilizing etch/passivation chemistries such as the cryogenic silicon etch (see, for example, reference 9) and SF6/C4F8 silicon etch (see, for example, reference 10), have enabled smooth and controllable sidewalls. Using electron beam lithography, resolution has improved to the tens of nanometers. Transferring such features to a substrate involves high quality of etch masks (see, for example, references 11-12). High selectivity of the resist will result in deeper etched features. A thicker resist may be used to achieve a greater etch depth trading off the maximum achievable resolution. A previously reported selectivity for cryogenic etch mask is 100:1 when using photoresist and 200:1 when using silicon dioxide (see, for example, reference 14).

Mechanical manipulation of micropillars and nanopillars using electro-static actuation (see, for example, references 20-21) involves a continuous supply of power to maintain deformation. A strain of less than 3% can be achieved (see, for example, reference 22-23) using deformation methods such as pseudomorphic growth. Given its impact on electronic as well as optical properties (see, for example, references 23-25), methods to accurately control strain are becoming increasingly popular in modern devices.

Anisotropic strain has recently been exploited as a method for breaking the inversion symmetry in silicon photonics (see, for example, references 24-25) introducing a second order non-linearity. Furthermore, such asymmetrically strained materials can exhibit interesting optical selection rules (see, for example, reference 23) based on the strained splitting of the degenerate light and heavy hole bands. Previously proposed methods to introduce strain typically rely on the deposition of lattice mismatched layers, a method which can incorporate a few percent of strain, and which is fixed at fabrication time (see, for example, references 22-23).

SUMMARY

According to a first aspect, a method for fabricating high aspect ratio probes is provided, comprising: providing a substrate comprising high aspect ratio pillars; coating the substrate with a resist and defining a metal pattern; depositing a metal layer on the resist; and lifting off the resist to create metal contacts for the high aspect ratio pillars and thereby forming the high aspect ratio probes.

According to a second aspect, a method for fabricating a high aspect ratio male-female connector is provided, comprising: providing a first substrate comprising a high aspect ratio pillar; coating the first substrate with a first resist and defining a first metal pattern; depositing a first metal layer on the first resist; lifting off the first resist to create a first structure, the first structure comprising the high aspect ratio pillar coated with a metal contact; providing a second substrate comprising a high aspect ratio hole; coating the second substrate with a second resist and defining a second metal pattern; depositing a second metal layer on the second resist; lifting off the second resist to create a second structure comprising the high aspect ratio hole coated inside with a metal layer; wherein during operation, a male-female connection is established by inserting the first structure into the second structure.

According to a third aspect, a method for fabricating high aspect ratio probes is provided, comprising providing a substrate; coating the substrate by a first resist; defining high aspect ratio pillars by patterning and exposing the first resist; developing the first resist; depositing an etch mask on the first resist; placing the first resist in a chemical bath to dissolve the resist and the etch mask; etching the substrate; removing a remainder of the etch mask to form high aspect ratio pillars; recoating the substrate with a second resist and defining a metal pattern; depositing a metal layer on the second resist;

and lifting off the second resist to create metal contacts for the high aspect ratio pillars and thereby forming the high aspect ratio probes.

According to a fourth aspect, a method for fabricating an array of high aspect ratio probes is provided, comprising: providing a substrate; coating the substrate with a first resist; defining high aspect ratio nanopillars by patterning the first resist; developing the first resist; depositing an etch mask on the first resist; coating the etch mask with a second resist different from the first resist; defining a placement of high aspect ratio micropillars by patterning the second resist; developing the second resist; performing a first etch to create the high aspect ratio micropillars; removing the second resist; placing the substrate in a chemical bath to dissolve the first resist and the etch mask; performing a second etch to initiate a generation of the high aspect ratio nanopillars; removing a remainder of the etch mask to form the high aspect ratio nanopillars on the high aspect ratio micropillars; and lifting off the third resist to create metal contacts for the high aspect ratio nanopillars and thereby generating the array of high aspect ratio probes.

According to a fifth aspect, a method for deforming pillars is provided, comprising: providing a plurality of pillars partially submerged in a resist; and contracting the resist in areas surrounding the plurality of pillars to deform the plurality of pillars.

According to a sixth aspect, a method for capturing small-scale objects is provided comprising: providing a plurality of small-scale objects surrounded by a plurality of pillars partially submerged in a resist; contracting the resist to bend the plurality of pillars inward to squeeze the plurality of small-scale objects and thereby forcing the plurality of small-scale objects through top of the plurality of pillars.

According to a seventh aspect, a method for fabricating high aspect ratio probes is provided, comprising: providing a highly doped silicon substrate; coating the substrate by a resist; defining the high aspect ratio probes by patterning and exposing the resist; developing the resist; depositing an etch mask on the resist; placing the resist in a chemical bath to dissolve the resist and the etch mask; etching the substrate; and removing a remainder of the etch mask to form the high aspect ratio probes.

According to an eighth aspect, a probe is provided, comprising: a plurality of nanopillars placed within controllable distances from one another; and a micropillar underlying the plurality of nanopillars.

According to a ninth aspect, a structure is provided, comprising a plurality of pillars partially immersed in a resist and deformed up to a 23.9% strain.

Further aspects of the present disclosure are shown in the descriptions, drawings and claims of the present application.

DETAILED DESCRIPTION

In what follows, methods for fabrication of high aspect ratio micropillars and nanopillars are described in accordance with various embodiment of the present disclosure. Here are definitions of some of the terms used throughout the present disclosure:

The term 'nano Pillar' means any pillar structure between 1 nm and 500 nm in width.

The term 'micropillar' means any structure between 1 μm and 500 μm in width.

The term 'aspect ratio' is defined a ratio of the height to the width of a micropillar, a nanopillar, a hole and/or a probe and the term 'high aspect ratio' intends to indicate an aspect ratio greater than ten.

The term 'probe' intends to indicate a pillar shaped conductive device used for measurement purposes by making an electrical contact.

Figure 1:
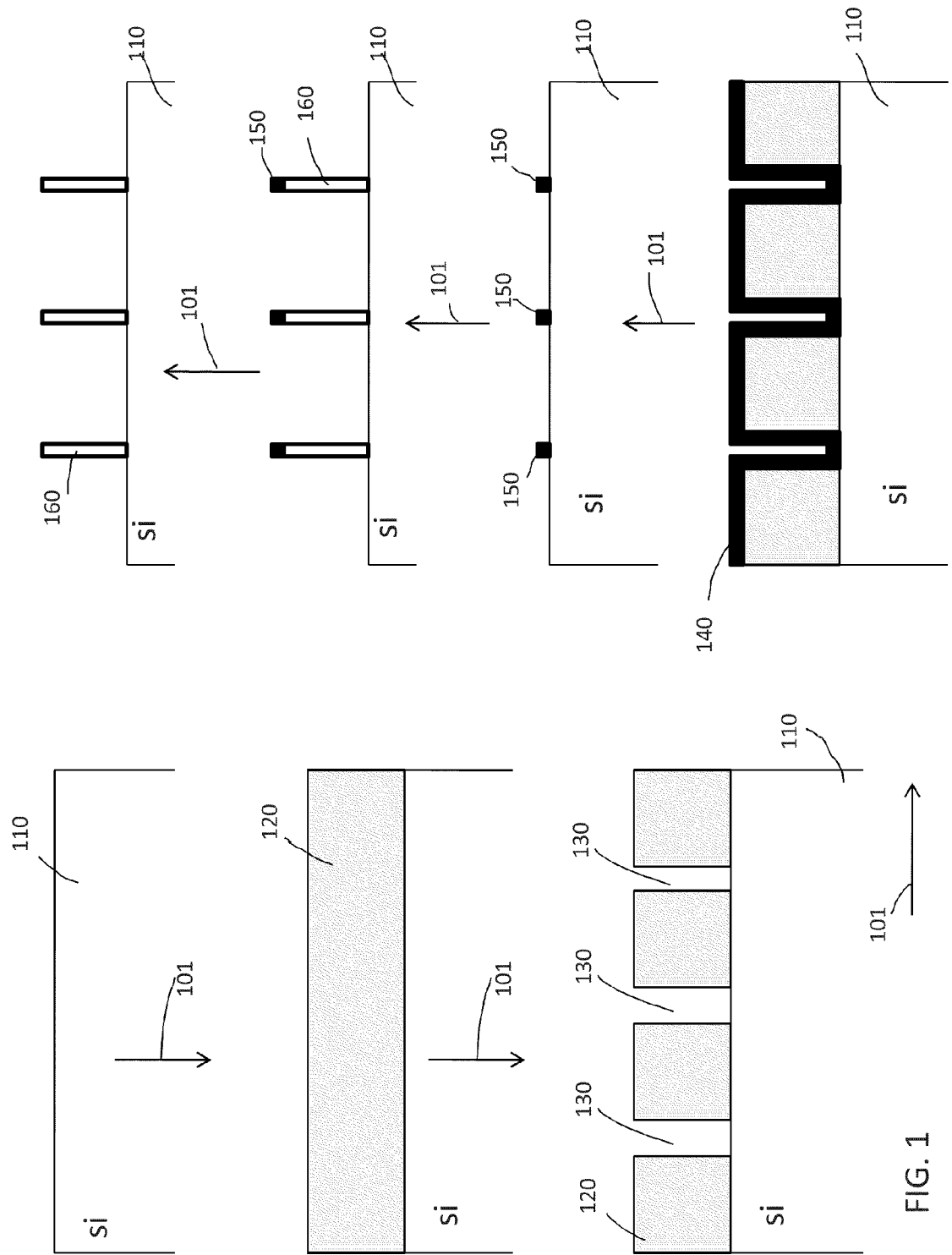
FIG. 1 shows fabrication steps of micropillars and nanopillars in accordance with an embodiment of the present disclosure.

According to an embodiment of the present disclosure, fabrication of both micropillars and nanopillars is performed using standard photo-beam and electron-beam lithographic techniques. FIG. 1 shows various steps of fabricating micropillars and nanopillars. A sequence of fabrication steps is indicated by arrows (101). For the sake of simplicity, throughout the present disclosure, the term 'pillar' intends to indicate both micropillars and nanopillars.

As shown in FIG. 1, a substrate (110) (e.g., a Si substrate) is provided and subsequently coated by a layer of resist (120). Patterns of high aspect ratio pillars (160) are lithographically defined and the resist (120) is then exposed (e.g., to ultraviolet 350 nm) and patterns are developed using a developer (e.g., MF 322). As a result, patterns comprising trenches (130) are generated. According to an embodiment of the present disclosure, in the scenario where micropillars are fabricated, the resist (120) can be a Clarion AZ 5214E spin-coated with a thickness of 1.6 micron. In a further embodiment where nanopillars are fabricated, Poly methyl methacrylate (PMMA) 950 A 2 is spun to a thickness of approximately 75 nm and exposed via a 100 kV electron beam. The PMMA is developed using a 1:3 mixture of Methly-Isobutyl-Ketone to isopropanol.

Figure 2:
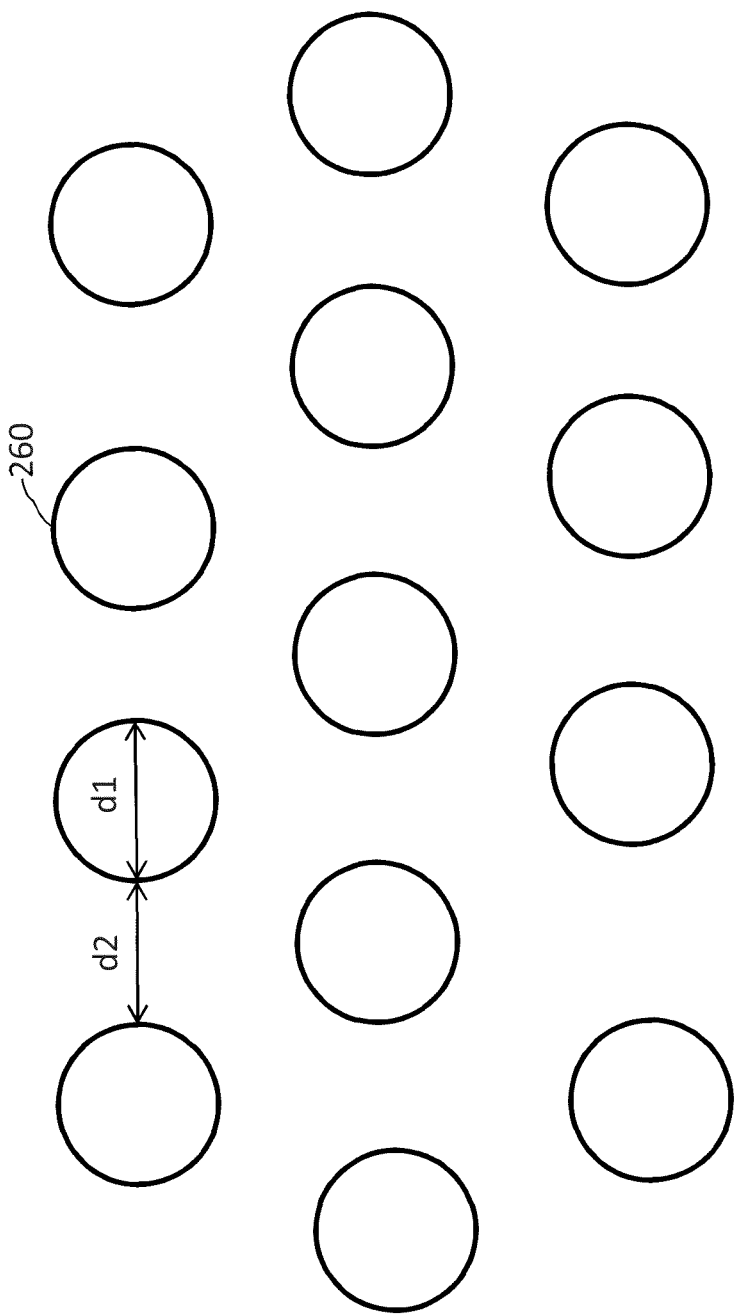
FIG. 2 shows an exemplary pattern for producing micropillars.

FIG. 2 shows an exemplary pattern for producing micropillars with circular cross-sections. The pattern shown in FIG. 2 is an array of hexagonally-packed pillars (260). The applicants fabricated such patterns wherein the pillars (260) had diameters d1 of 5, 10, 20, and 50 microns with a controlled spacing d2 between the pillars (260) equal to d1. The person skilled in the art will understand that other embodiments, where patterns are of arbitrary cross-sections and arrangements, can be provided wherein a spacing among pillars is controlled.

Continuing with the description of the fabrication process described with reference to FIG. 1, in accordance with an embodiment of the present disclosure, an etch mask (140) is then deposited on the patterned substrate (110). To produce the etch mask (140), the applicants used a TES 1800 DC magnetron sputter system, using a 99.995% aluminum target and a 5:1 mixture of argon to oxygen as the process gas. The persons skilled in the art will appreciate that this ratio of gases allows for the aluminum to be sputtered without poisoning the target while still depositing a stoichiometric alumina. Throughout the present disclosure, the term 'stoichiometric' intends to indicate a composit material containing the natural ratio of its constituent atoms. As an example, Silicon Dioxide contains silicon and oxygen atoms in a ratio of 1:2 as the chemical formula is SiO2. According to a further embodiment of the present disclosure, at 400 watts DC power, alumina was deposited at an approximate rate of 10 nm per minute.

Further referring to FIG. 1 and continuing with the description of the fabrication steps described above, the coated substrate (110) is then placed in a chemical bath (e.g., acetone or a mixture of acetone and dichloromethane when fabricating respectively micropillars or nanopillars) where the resist (120) and the etch mask (140) (e.g., alumina) are dissolved, leaving only masking disks (150) on the substrate (110). The person skilled in the art will appreciate that as alumina is brittle, the etch mask (140) fractures as the resist is swelled in the chemical bath and this results in an easier lift off and therefore an improved feature transfer.

With continued reference to FIG. 1, etching of the substrate (110) is then performed to produce the high aspect ratio pillars (160) underlying the masking disks (150). The applicants used Oxford Instrument's PlasmaLab System100 ICP-RIE 380s to perform etching. According to some embodiments of the present disclosure, two different fluorinated etch chemistries can be utilized: a $SF_6/O_2$ cryogenic etch, which is more chemical in nature and the Pseudo Bosch ($SF_6/C_4F_8$), which involves more physical milling than the cryogenic etch. Throughout the present disclosure, the term 'Pseudo Bosch' intends to indicate an etching that involves $SF_6$ and $C_4F_8$ wherein both gases are injected simultaneously. Both etch chemistries utilize a simultaneous etching and passivation technique, allowing for precise control over the etch anisotropy. The applicants used the $SF_6/O_2$ cryogenic etch for the creation of micropillars and the Pseudo Bosch ($SF_6/C_4F_8$) to fabricate nanopillars. The person skilled in the art will understand that other etching methods such as inductively coupled plasma (ICP), reactive ion etch, electron cyclotron etch (ECR), chemically assisted ion beam etch and wet etching can also be used.

As shown in FIG. 1, the masking disks (150) are then removed to generate high aspect ratio pillars (160). In accordance with embodiments of the present disclosure, a removal of the masking disks (150) can be performed using either buffered hydrofluoric acid or ammonium hydroxide mixed with hydrogen peroxide (known in industry as RCA-1 cleaning.) These removal methods have minimal impact on the substrate (110).

Figure 3:
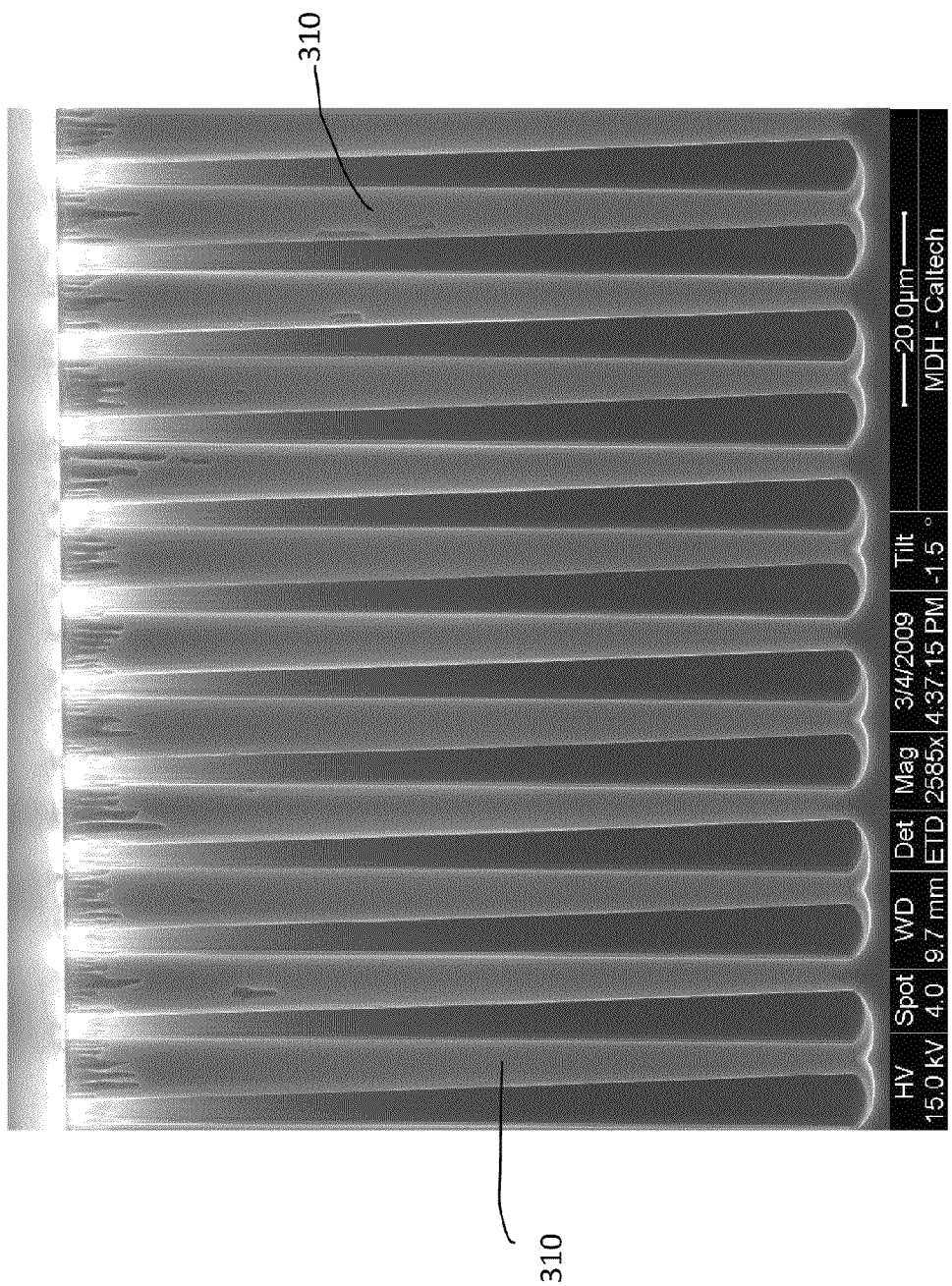
FIG. 3 shows a cross-section SEM image of micropillars.

Cryogenic etching achieves etch rates of several microns per minute, facilitating a fabrication of large structures. As shown in FIG. 3, the applicants fabricated pillars (310) with aspect ratios greater than 12 and etch depths up to 150 microns. FIG. 3 shows a cross sectional SEM image of 5 micron diameter silicon pillars (310) cryogenically etched to a height of 83 microns and masked using 110 nanometers of alumina, displaying a selectivity of approximately 755:1 and aspect ratio of 25. As shown in FIG. 3, the pillars (310) are 1.4 degrees reentrant. Throughout the present disclosure, the term 'selectivity' is defined as the ratio of a maximum achievable etch depth in a substrate to the ratio of the etch mask employed. An ICP power of 900 W combined with a RIE power of 3 to 9 W established a strong chemical etch with minimal milling. A 10 to 1 ratio of $SF_6$ to $O_2$ balances the etch and passivation rates to provide sidewall angles of 88 to 91 degrees.

Figure 4:
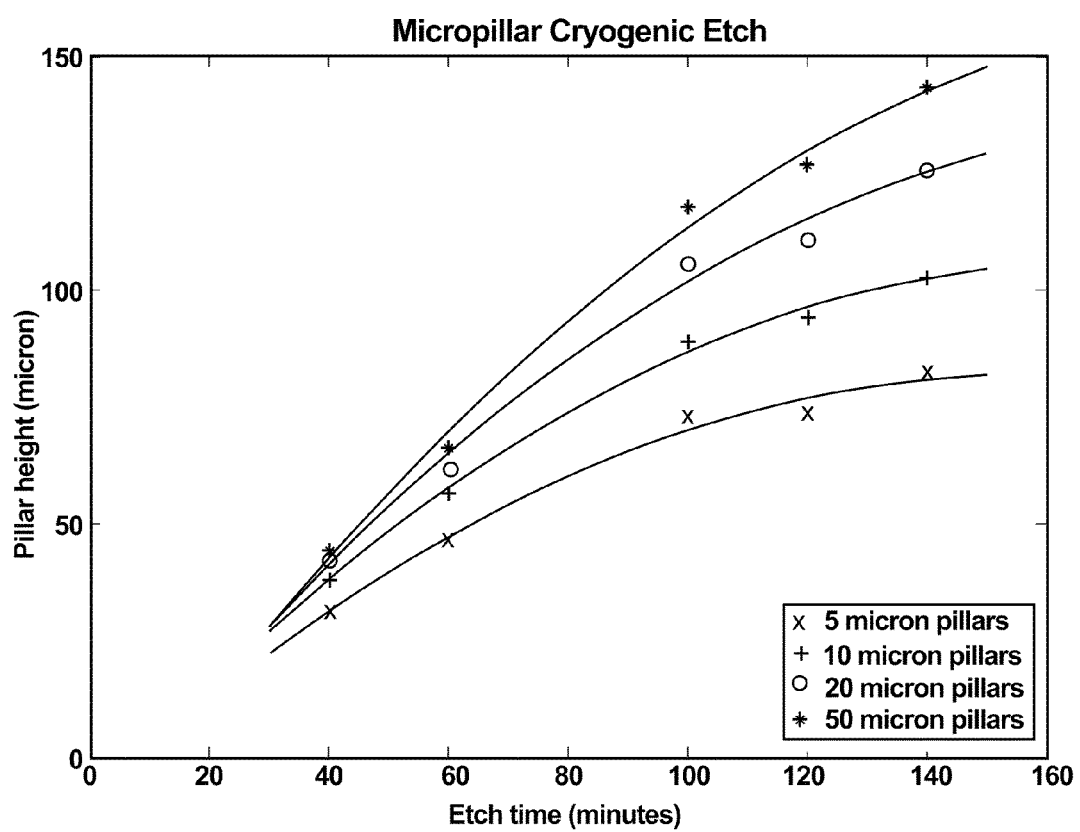
FIG. 4 shows plots of pillar height vs. etch time when fabricating micropillars.

According to various embodiments of the present disclosure, for each set of 5-50 micron diameter pillars, etch depths between 50 and 160 microns can be achieved by varying the etch time as shown in plots of FIG. 4. Furthermore, a surface roughness 20 nanometers can also be achieved. Throughout the present disclosure, the term 'surface roughness' is defined as the maximum height or width of irregularities found on the surface of an etched structure. An increase in separation between curves with an increase in etch time can also be seen in FIG. 4. This is an indication of etch dependence on aspect ratio. Moreover, etch rates, corresponding to the slope of the curves, are also noted to decrease as the aspect ratio increases. Referring to FIG. 4, one can further note that etch rates begin to diverge across pillar diameters and decrease as the etch continues deeper into substrate. This shows that as the aspect ratio of the etch increases, the etch rate decreases in a manner similar as demonstrated previously using a Bosh etch (see, for example, reference 13).

Figure 5A:
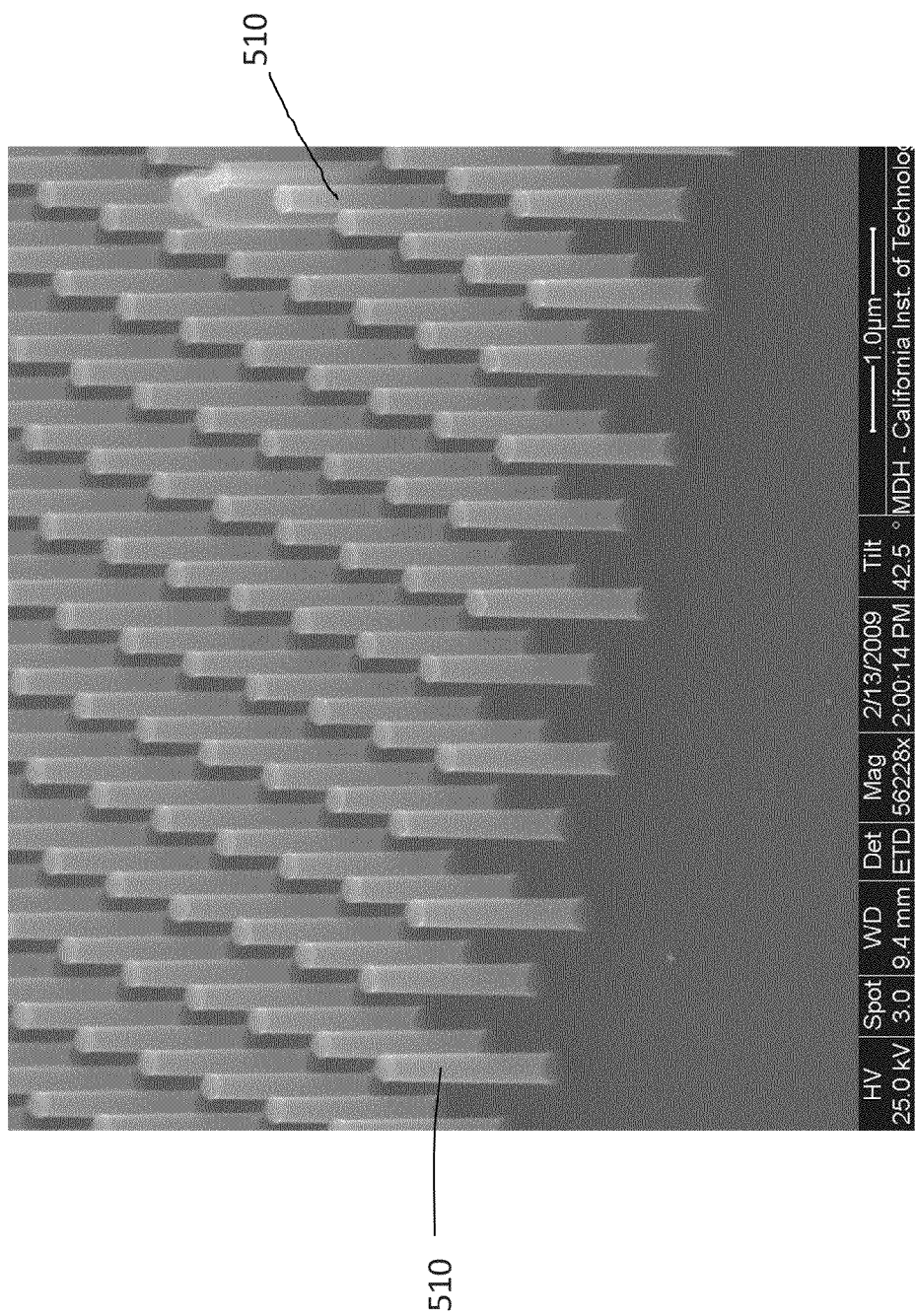
FIG. 5A shows a cross-sectional SEM image of nanopillars.
Figure 5B:
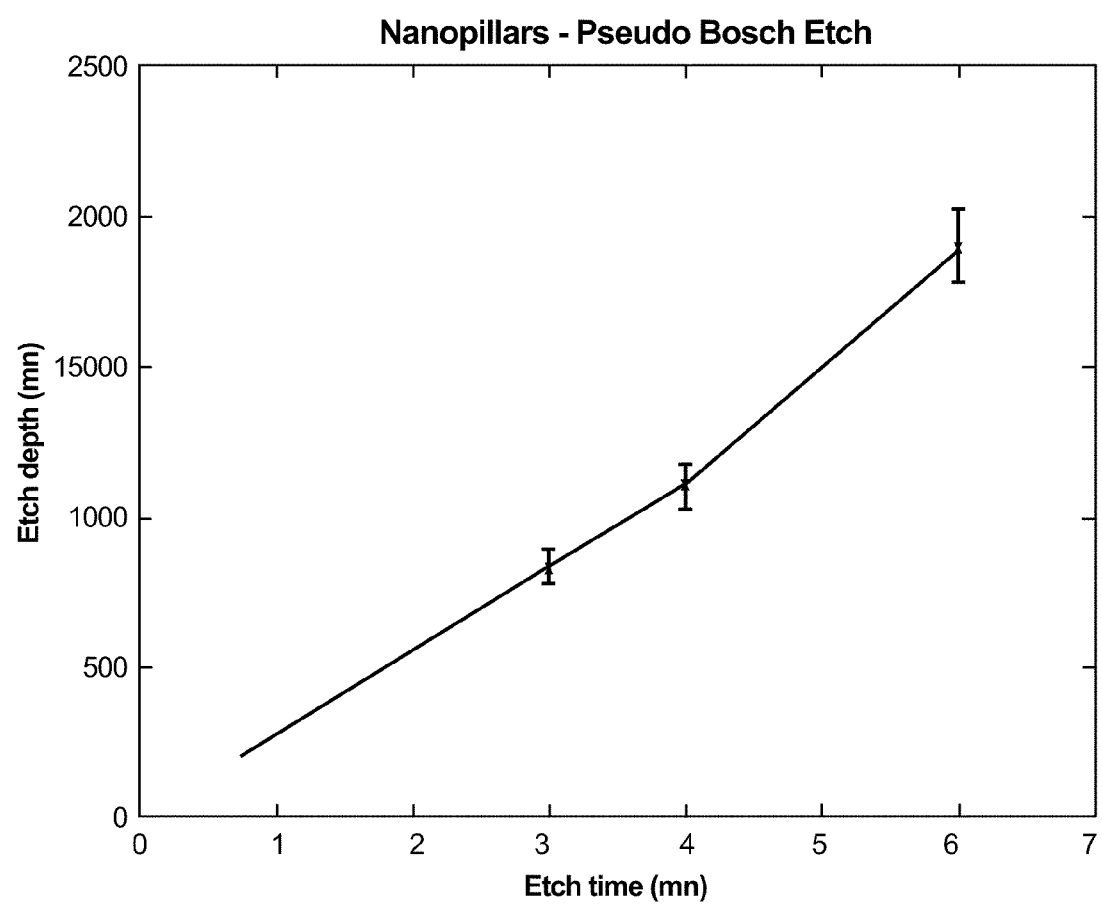
FIG. 5B shows a plot of pillar height vs. etch time when fabricating nanopillars.

FIG. 5A shows SEM image of 150 nanometer diameter silicon pillars (510) etched to a height of 1.2 microns using the Pseudo Bosch etch and masked using alumina with a thickness of 30 nm. Various pillar diameters, ranging from 30 nm to 250 nm, were arranged on a sample and etched simultaneously. FIG. 5B shows a plot of pillar height vs. etch time. Error bars in the plot of FIG. 5B indicate a range of etch depths for different pillar diameters. This demonstrates that aspect ratio has minimal effects on nanopillars as compared to micropillars. The applicants used an ICP power of 1200 W combined with a RIE power of 20 W where a balanced chemical/mechanical etch was established. Since this etch is slower than the cryogenic etch, it provides improved control over etch depth for creating nanopillars. The applicants fabricated nanopillars with aspect ratios of over 25 and pillar diameters from 30 nm to 200 nm. Vertical sidewalls are achieved using a $SF_6$ to $C_4F_8$ ratio of 33:57. Moreover, the applicants produced Pillar heights of over 2 microns with no noticeable notching.

Figure 6:
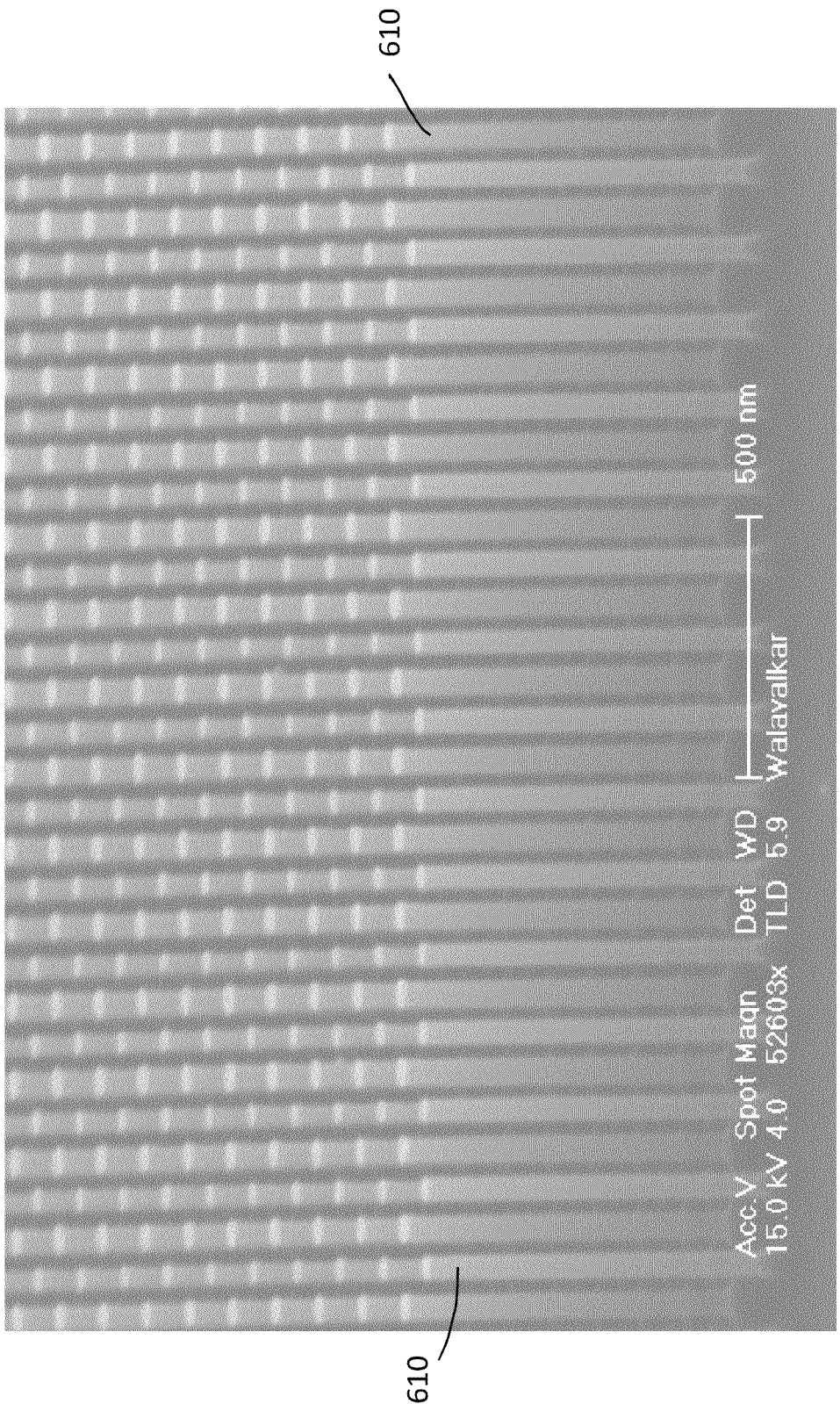
FIG. 6 shows another cross-sectional SEM image of nanopillars.

FIG. 6 shows an SEM image of alternating rows of 40 and 65 nanometer diameter silicon pillars (610) etched to a height of 780 nanometers using the Pseudo Bosch etch with a 30 nanometers thick alumina etch mask according to an embodiment of the present disclosure.

Figure 7:
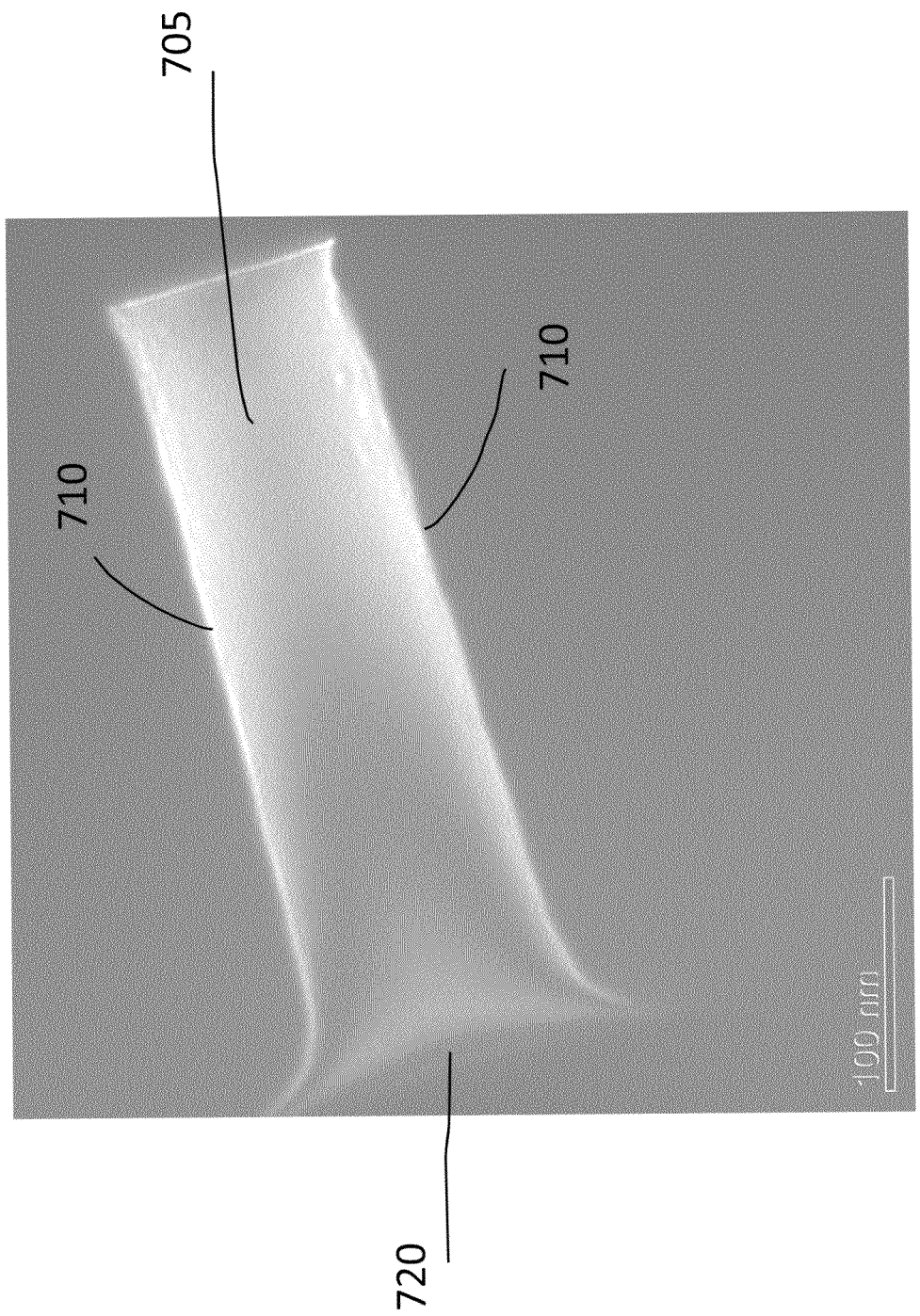
FIG. 7 shows a transmission electron micrograph of a nanopillar.

FIG. 7 shows a transmission electron micrograph of a 100 nm wide nanopillar (705). As can be seen in FIG. 7, etch sidewalls (710) are straight with little undercut and no notching at a base (720). The image shown in FIG. 7 was generated using bright field reflection electron microscopy in a FEI transmission electron microscope. Surface roughness on the 100 nm diameter pillar (705) is estimated to be less than 5 nm. The image shown in FIG. 7 is rotated approximately 60 degrees clockwise.

With reference to FIG. 1, in what follows, some details regarding alumina used as the etch mask (140) are described.

Stoichiometry of a sputtered alumina is determined using energy dispersive X-rayspectroscopy (EDX) and a resulting spectrum. As shown in FIG. 8B, in accordance with an embodiment of the present disclosure, an analysis of the spectrum indicates that the etch mask (140) of FIG. 1 is within 0.6% of stoichiometric alumina with a ratio of oxygen to aluminum very nearly 3:2. DC resistance measurements of the alumina further ensure the etch mask (140) of FIG. 1 is electrically insulating rather than conducting, as aluminum is. The electrically insulating feature of the etch mask (140) avoids potential notching. Furthermore, a use of alumina resulting an easy removal. According to an embodiment of the present disclosure, an alumina layer can be stripped using buffered hydrofluoric acid at a rate of approximately 12 nm per minute.

With further reference to FIG. 1, according to an embodiment of the present disclosure, a use of alumina as the etch mask (140) for fluorinated silicon etch chemistries will provide a selectivity of as high as 5000:1. In another embodiment, for the cryogenic etch, a 26 nm thick alumina mask can be used to etch more than 100 microns into a substrate.

Figure 8A:
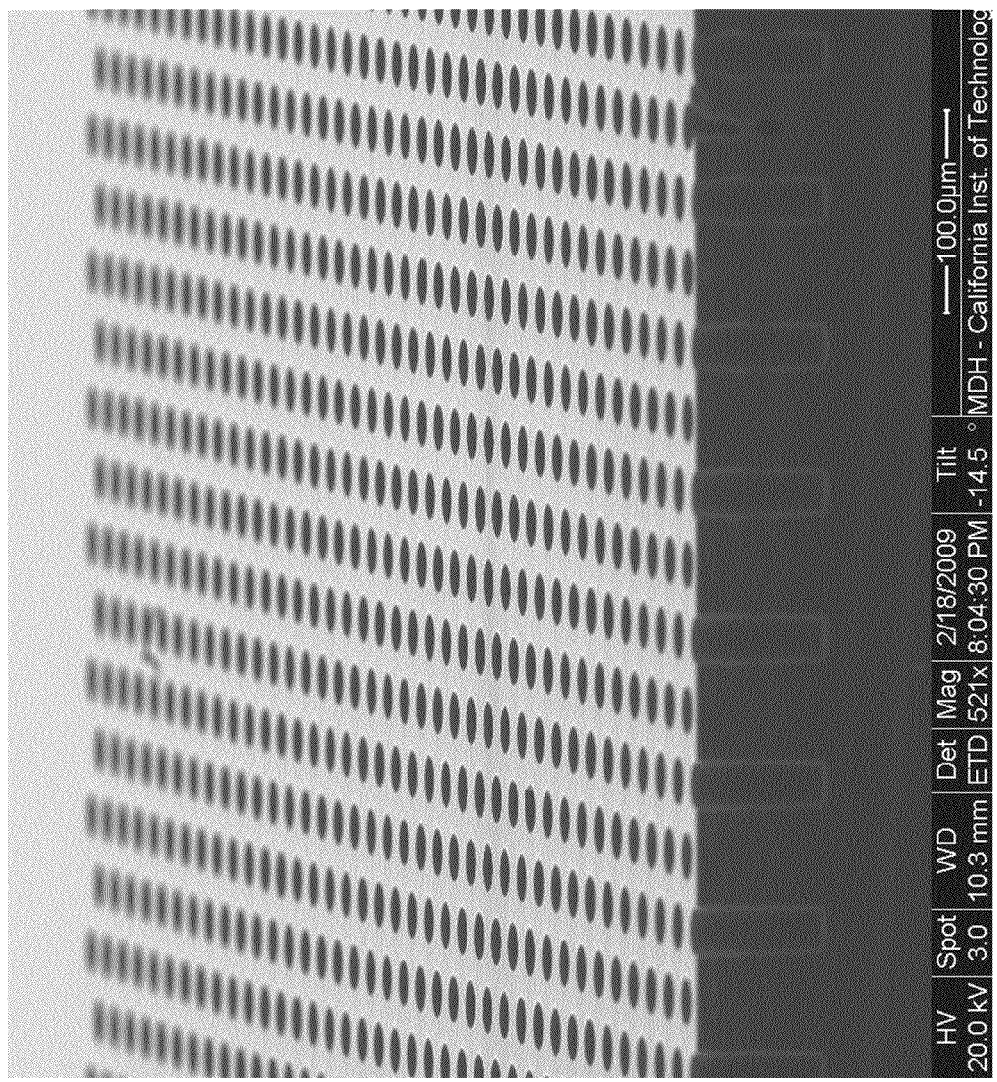
FIG. 8A shows an array of high aspect ratio holes.
Figure 8B:
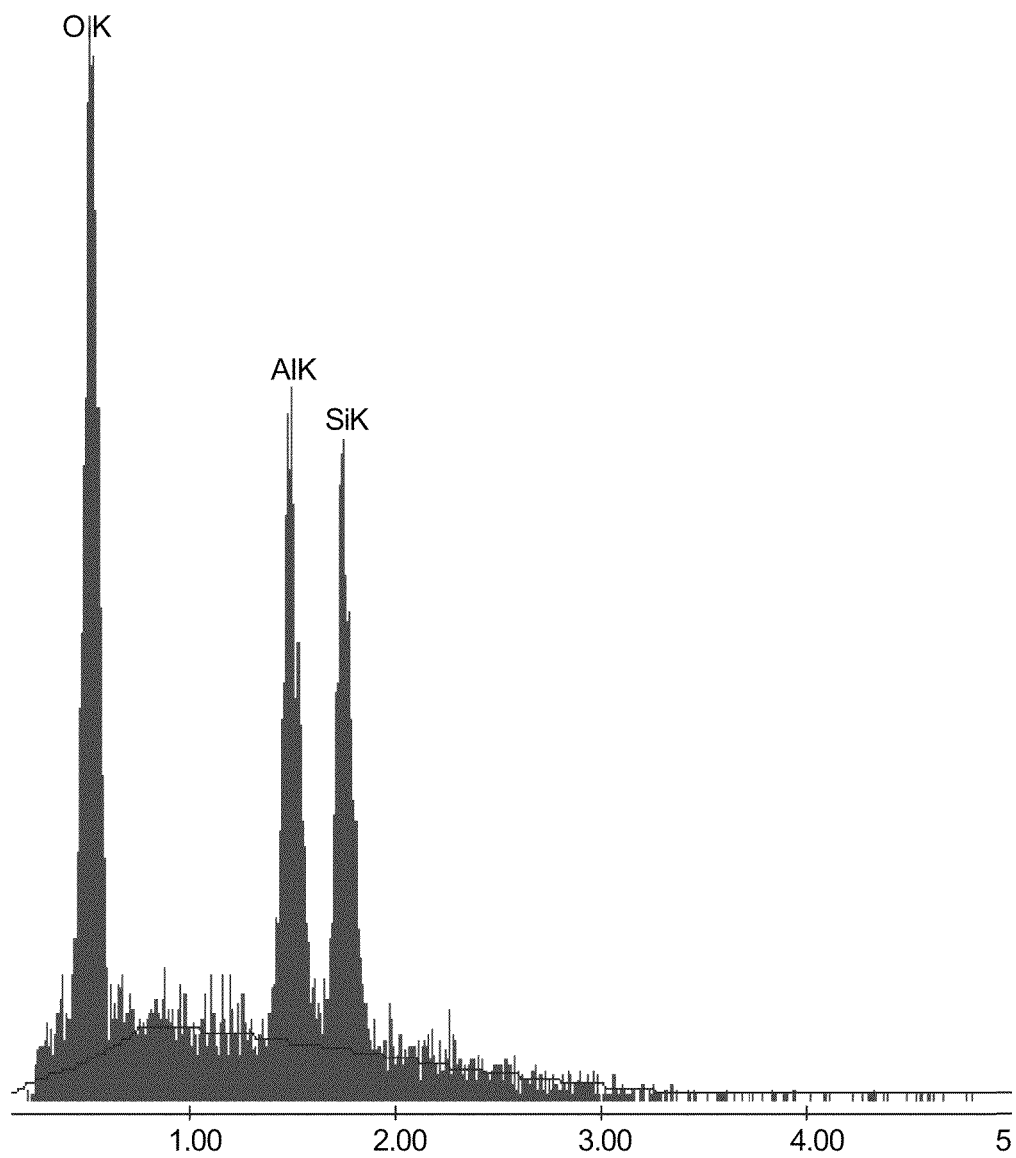
FIG. 8B shows a spectrum using energy dispersive X-ray spectroscopy (EDX).

FIG. 8A shows an array of 20 micron diameter holes (810) etched 64 microns deep and spaced 20 microns apart. The arrays of the holes (810) shown in FIG. 8A was fabricated using a method substantially similar to the fabrication method describe with reference to FIG. 1. An alumina etch mask of less than 20 nanometers thick was used yielding a selectivity of 3200:1. As shown in FIG. 8B, an energy-dispersive x-ray analysis (EDAX) spectrum (not shown) was taken of the alumina etch mask displaying a measured ratios of oxygen to aluminum of 1.4906; 0.6% of stoichiometric alumina.

In accordance with other embodiments of the present disclosure, using the Pseudo Bosch etch chemistry, an alumina etch mask of 25 nm, 80 nm diameter pillars were etched to heights of 1.7 microns yielding a selectivity of better than 68:1.

Referring to FIG. 1, the described fabrication sequence can be used to produce devices such as probe tips, male and female mating components, and probe cards. In what follows, fabrication of such devices and related methods are described.

Figure 9B:
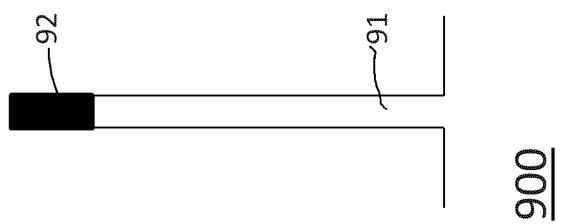
FIGS. 9A-B show exemplary embodiments of a probe.
Figure 9A:
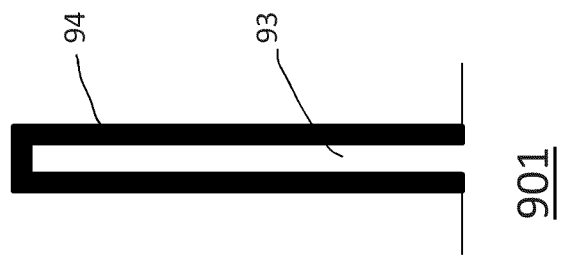

FIGS. 9A-B show two exemplary embodiments of a probe (900, 901). The probe (900) comprises a metal pad (92) formed on a pillar (91) and the probe (901) comprises a pillar (93) coated with a metal layer (94). In accordance with an embodiment of the present disclosure, the pillar (93) can have a diameter of 50 nm and the metal layer (94) can be 20 nm thick. Embodiments can be envisaged wherein the probe (901) can be inserted into a high aspect ratio hole coated with metal layer, thus forming a male-female connector.

Referring to FIGS. 9A-B, in some embodiments, in order to generate the metal pad (92) or the metal layer (94), a resist (e.g., photo-resist or electron-beam resist) can be used to define a metal pattern. This is followed by depositing metal and then lifting off the resist to produce the metal pad (92) or the metal layer (94). This allows for probes to be mass produced with precision alignment using lithographic techniques. By way of example and not of limitation, techniques such as plasma sputtering, electroplating and metal evaporation can be used for metal deposition.

Using methods similar to the one described with reference to FIG. 1, in accordance to further embodiments of the present disclosure, a highly doped Si is used to generate a probe. As such, when the probe makes contact with an external metal, an Ohmic contact is made allowing a signal to be transferred from the external metal to the probe.

Height of probes fabricated based on the above-mentioned methods can be further extended using methods described below in accordance with some embodiments of the present disclosure.

Figure 10:
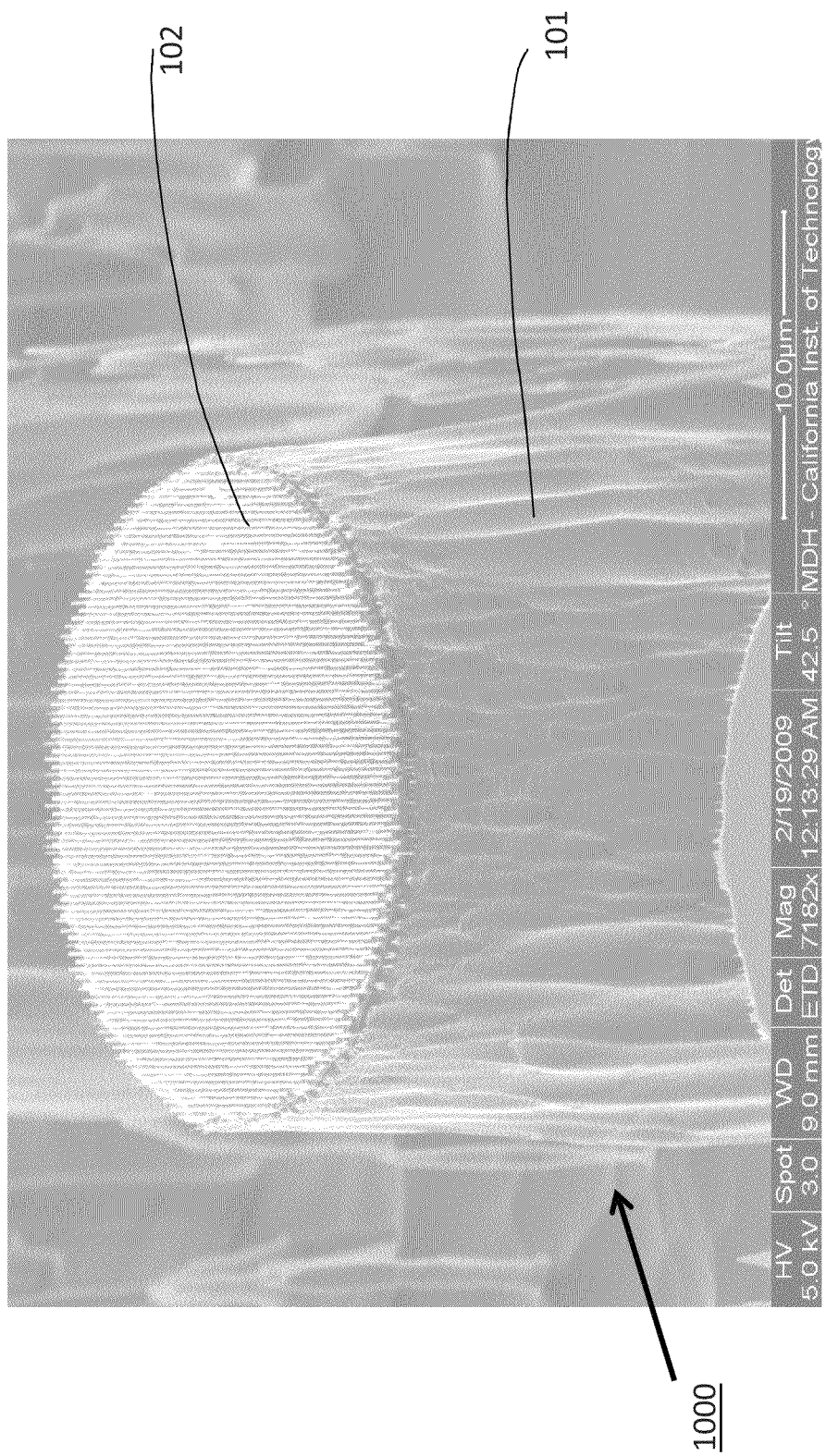
FIG. 10 shows a structure comprising a micropillar underlying a plurality of nanopillars.

FIG. 10 shows a structure (1000) comprising a micropillar (101) underlying a plurality of nanopillars (102). According to an embodiment of the present disclosure, the nanopillars (102) can be 1 micron tall with a diameter of 100 nm. In accordance with a further embodiment of the present disclosure, fabrication of the structure (1000) can be performed in two etching steps and using fabrication steps substantially similar to the ones described with reference to FIG. 1. Patterns corresponding to the nanopilars (102) are first defined using a first resist (e.g., electron-beam). This is followed by deposition of an etch mask (e.g., alumina). Subsequently, patterns related to the micropillar (101) are defined using a layer of a second resist (e.g., photoresist), different from the first resist, the layer of the second resist covering the patterns related to the nanopillars (102). A first etch (e.g., cryogenic) is then performed to create the micropillar (101) and the layer of the second resist is subsequently removed. This is followed by performing a second etch to produce the nanopillars (102). A remainder of the etch mask is then removed to produce the structure (1000) of FIG. 10.

In what follows, controllable deformation of micropillars and nanopillars and related methods are described in accordance with several embodiments of the present disclosure.

In order to demonstrate deformation of pillars, a sample comprising an array of pillars on a substrate is provided. The array of pillars is then coated with a layer of polymer serving as resist. The layer of polymer is then planarized (e.g., using an oxygen plasma) to achieve a desired resist height. According to some embodiments of the present disclosure, a volumetric contraction of the resist can be used to selectively deform pillars. It has been noted (see, for example, references 26-27) that under high electron beam doses (e.g., approximately ten times the standard dose used in electron-beam lithography) an originally positive-tone PMMA cross-links, i.e., behaves as a negative resist. Throughout the present disclosure, the term 'standard dose' for Poly-methl-Methacrylate (PMMA) intends to indicate a quantity of 1000-1400 microCoulombs/cm^2. Along with this change in resist tone, cross-linking causes a volumetric contraction of the resist. Applicants used PMMA as the resist wherein a selective deformation of the pillars was performed using the above-described volume contraction of the PMMA. Throughout the present disclosure, the term 'cross-link' intends to indicate a scenario wherein one organic molecule links to another organic molecule. As an example, PMMA molecules bind together with Carbon-Carbon bonds to make other PMMA molecules. According to further embodiments of the present disclosure, a force exerted by the PMMA on the pillars can be tuned by varying an electron beam-exposure, heating, and selective polymer removal resulting in controllable and reversible bending and straining of the pillars. Due to the stability of PMMA at room temperature, a configuration of deformed pillars remains fixed, enabling further electrical or mechanical tests to be performed on the sample while under strain.

Figure 11:
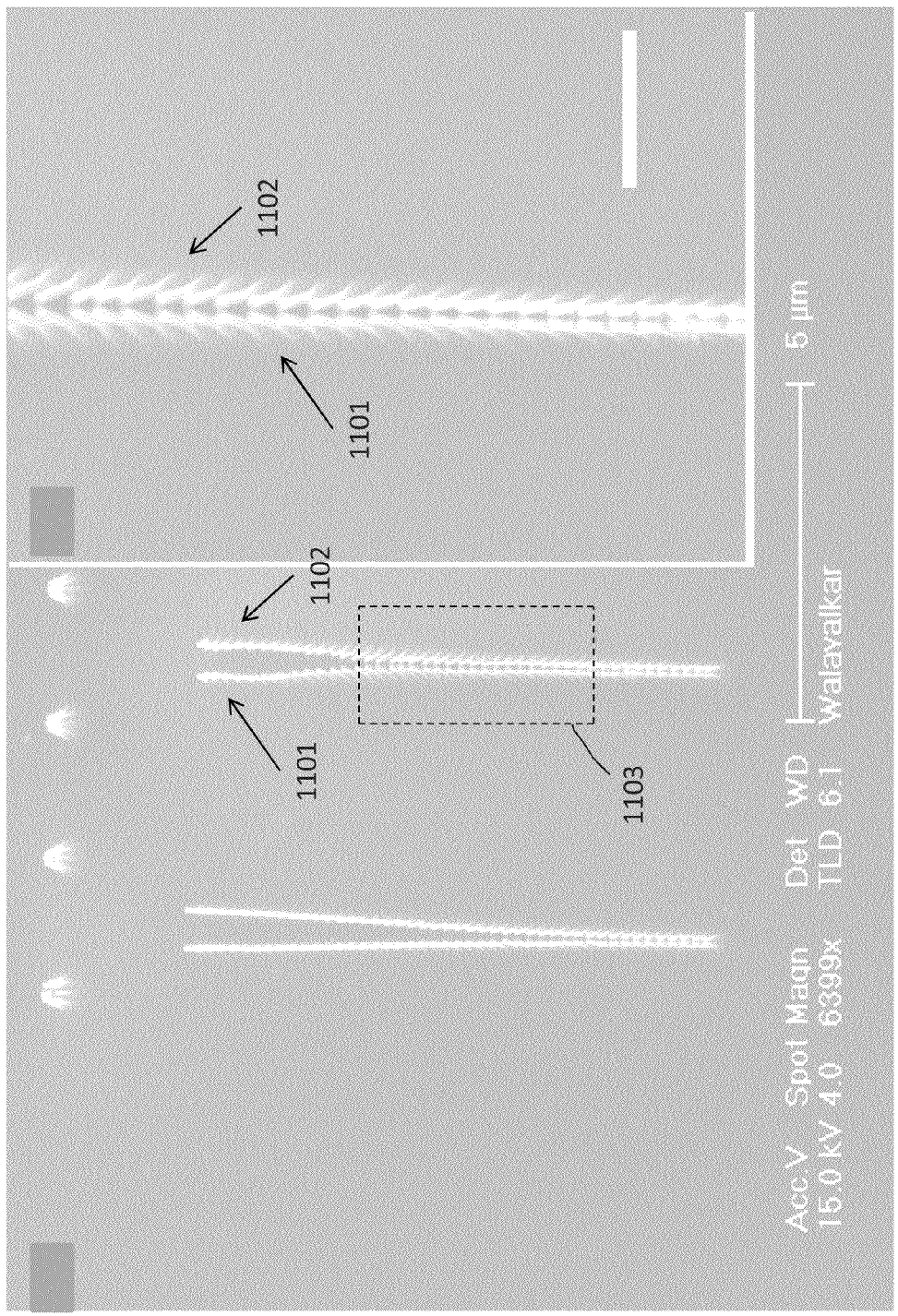
FIG. 11 shows strips of deformed pillars.

FIG. 11 show two strips of nanopillars (1101, 1102) fabricated using the methods described with reference to FIG. 1.

The two strips of nanopillars (1101, 1102) are 75 nm thick and submerged into a 300 nm thick PMMA. In accordance with an embodiment of the present disclosure, by exposing only a section of the strips of nanopillars (1101, 1102), i.e., nanopillars shown inside a dashed rectangle (1103), cross linking of PMMA occurs and those nanopillars shown inside the dashed rectangle (1103) are pulled inward. This is also shown in more detail in a right hand side inset of FIG. 11. A length of exposure dictates an electron dose and hence an amount of contraction between nanopillars. Since the Applicants performed exposure in an SEM, they could view the progress of deformation in real time, freeze exposures, take measurements and continue until a desired exposure was obtained. Using this process, a precision equal to SEM resolution is achievable in the final positioning of the strips of nanopillars (1101, 1102).

Figure 12A:
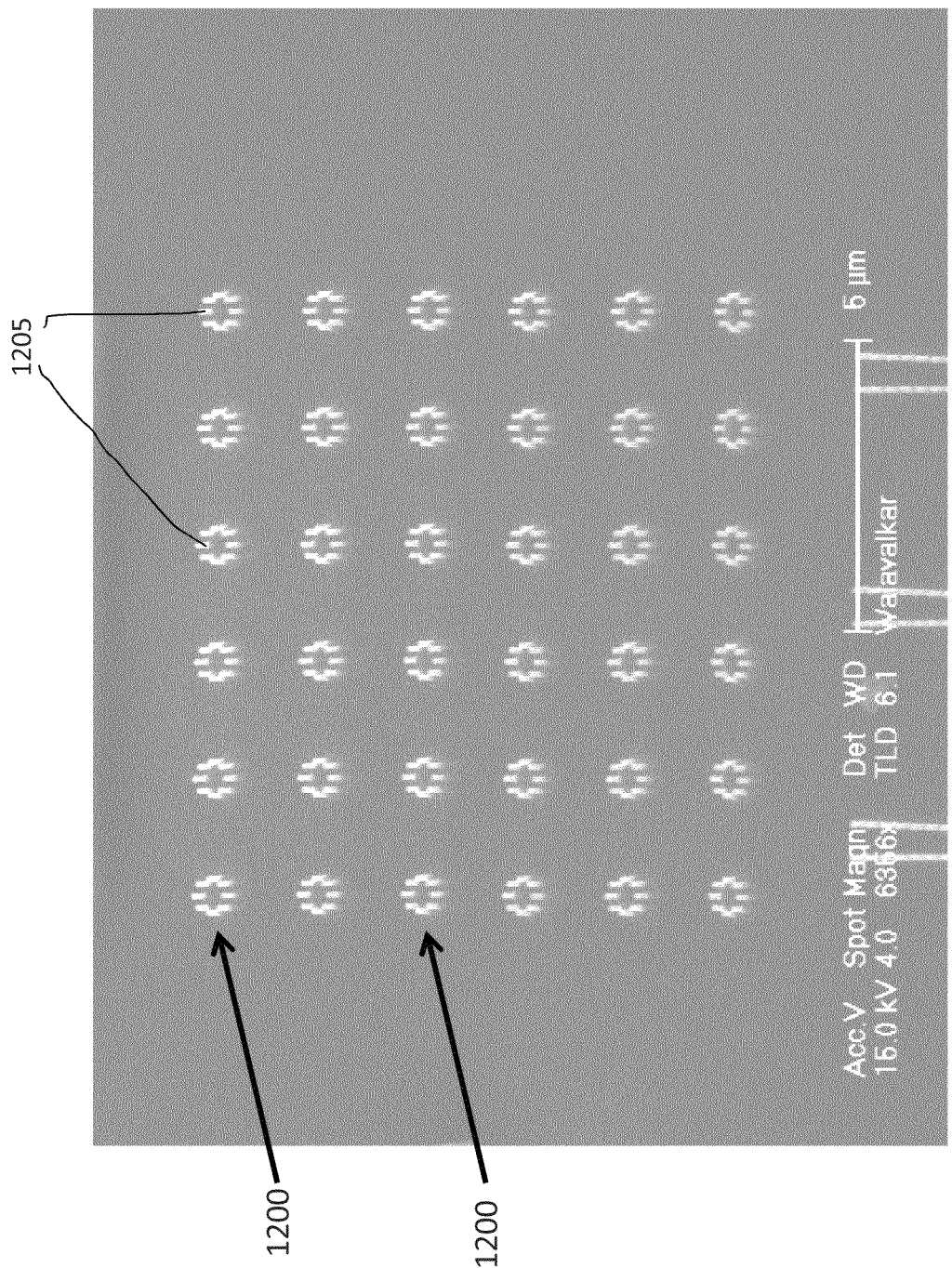
FIG. 12A shows rings of nanopillars.
Figure 12B:
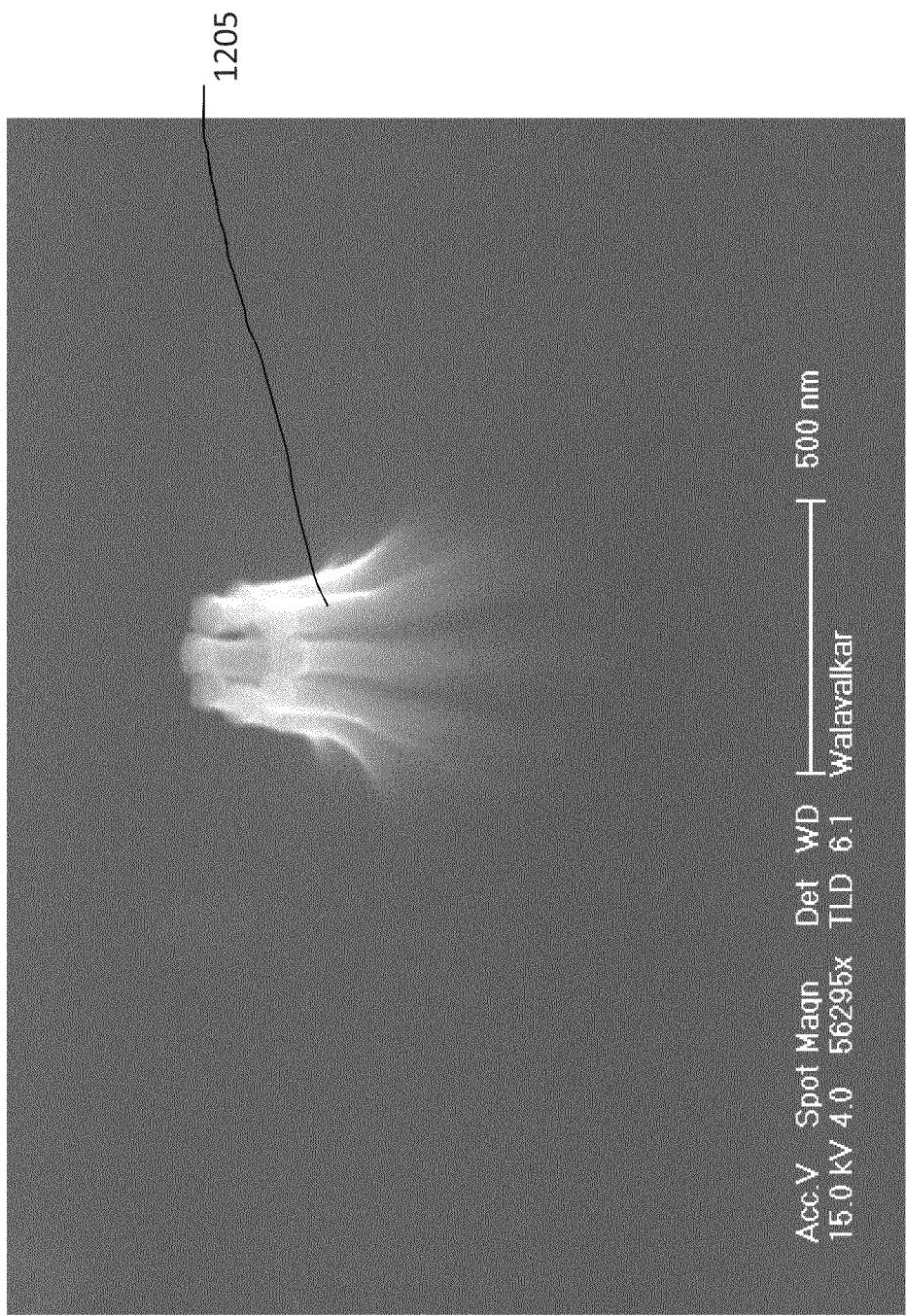
FIG. 12B shows one of the rings of FIG. 12A after being deformed.

FIG. 12A shows rings (1200) of eight nanopillars (1205) fabricated based on the methods described with reference to FIG. 1. The nanopillars (1205) are 75 nm in diameter and 800 nm tall. The rings were initially 500 nm in diameter with 230 nm circumferential spacing between the nanopillars (1205). A central region of the rings (1200) were exposed in SEM, yielding a uniform radial deformation of the nanopillars (1205). Contraction terminated when the nanopillars (1205) were flush, with a final diameter of 184 nm after exposure. FIG. 12B shows one of the rings (1200) after contraction.

Figure 13A:
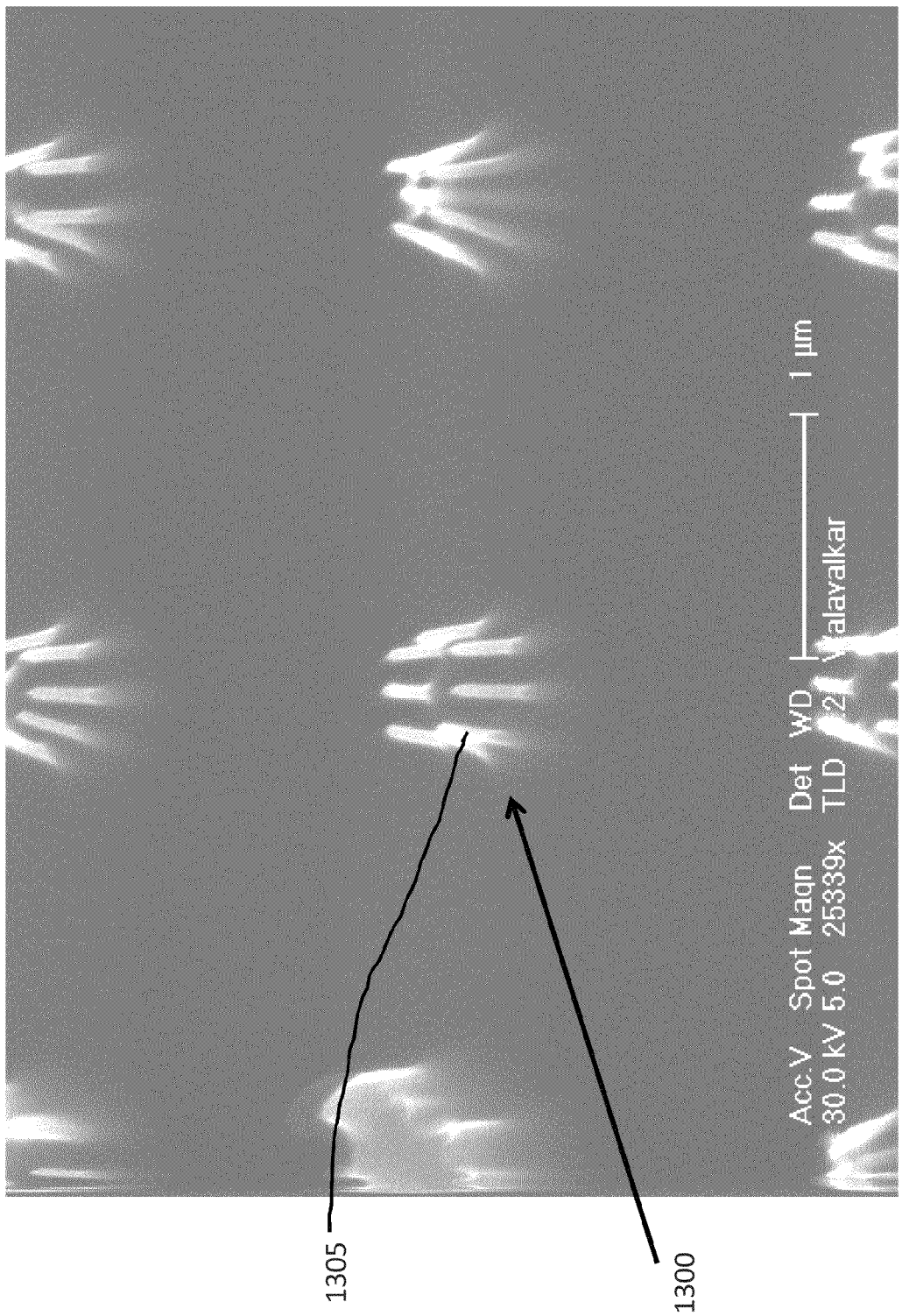
FIG. 13A shows a ring of nanopillars before deformation.
Figure 13B:
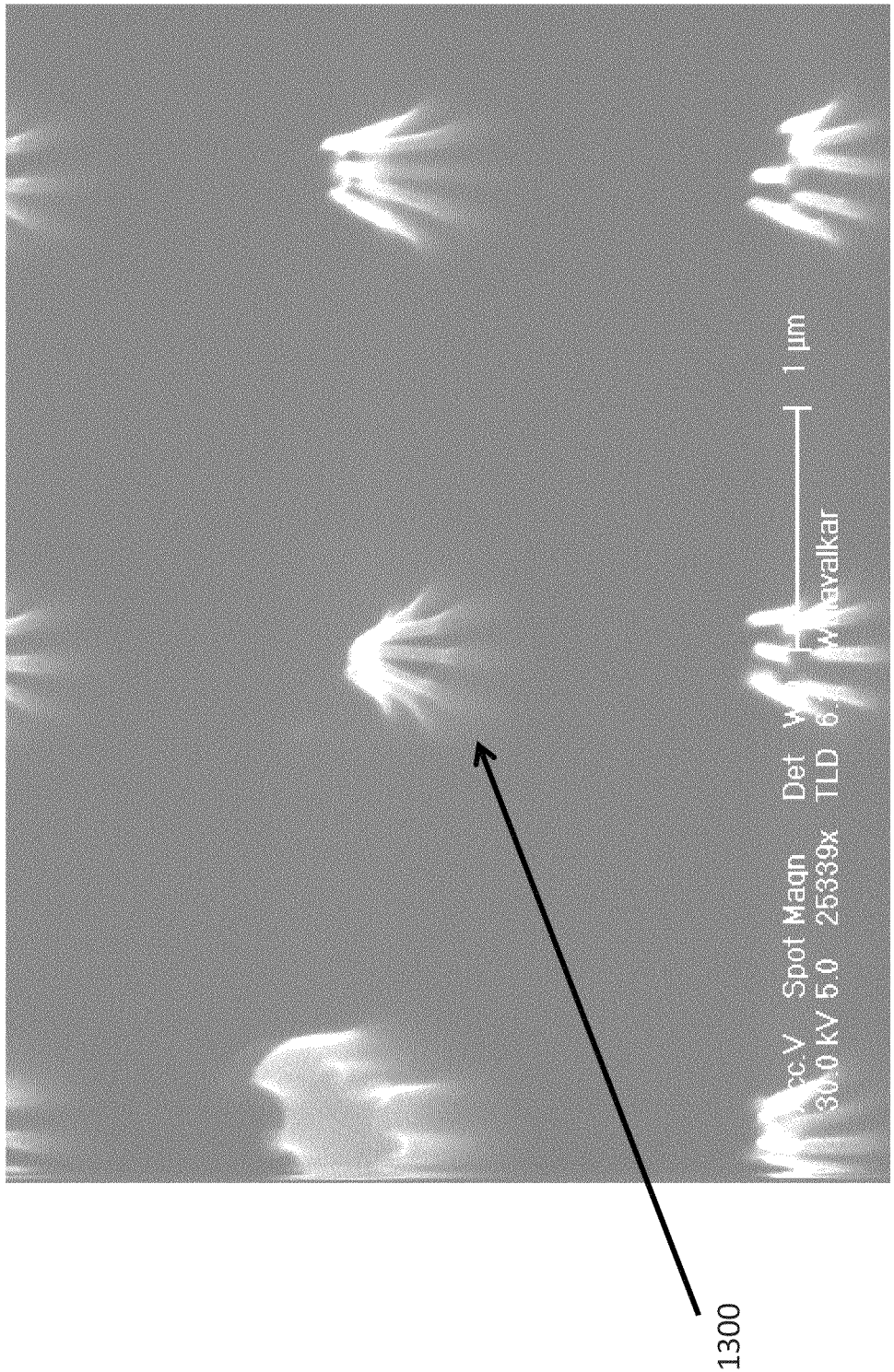
FIG. 13B show the ring of FIG. 13A after deformation.
Figure 13C:
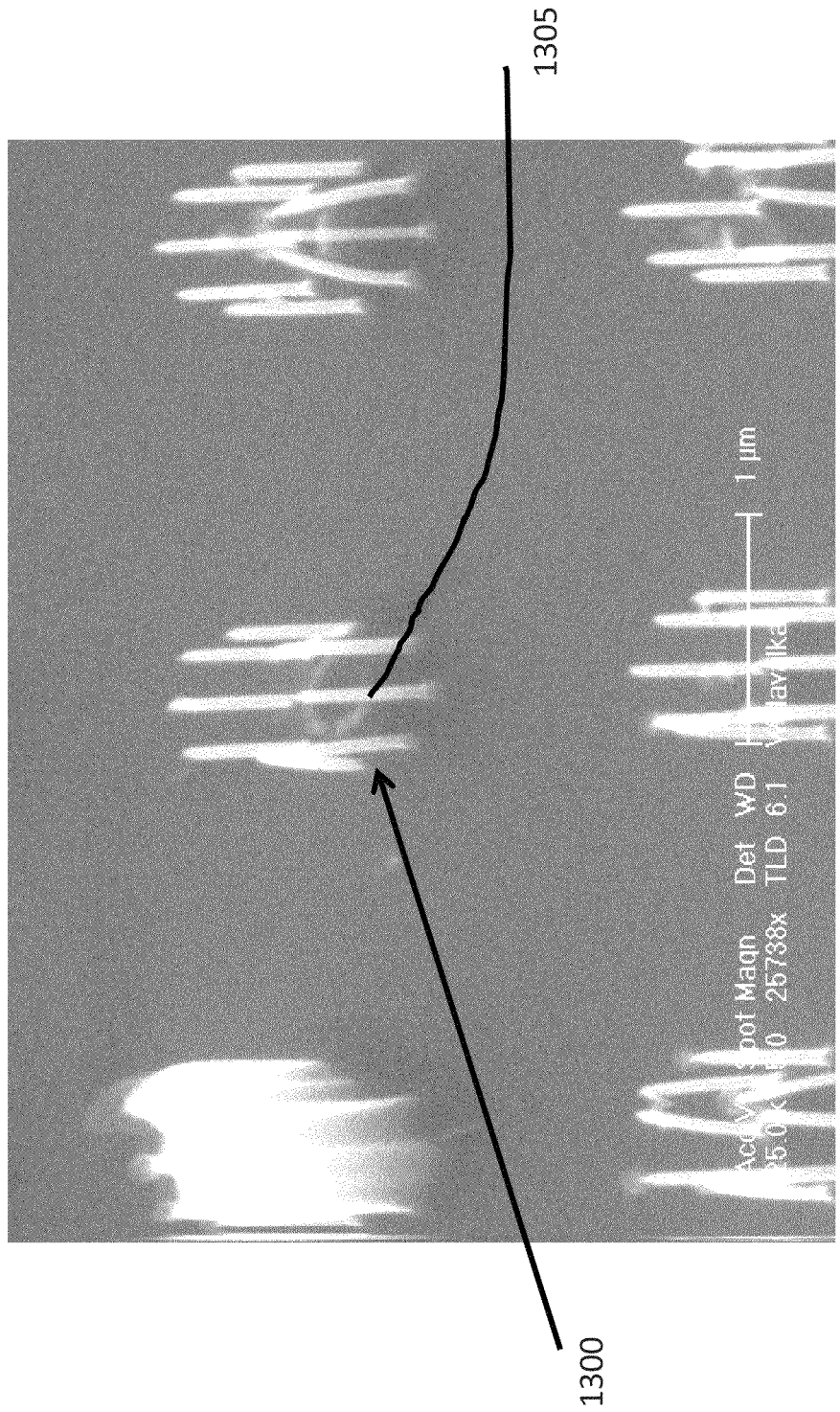
FIG. 13C shows the ring of FIG. 13B after oxygen plasma release.

FIG. 13A shows a ring (1300) of eight nanopillars (1305) fabricated based on the methods described with reference to FIG. 1. The ring (1300) has a diameter of 500 nm. The nanopillars (1305) are 50 nm in diameter and 1 μm tall. Using the same methods as described with reference to FIGS. 11-12, a deformation of the nanopillars (1305) was performed until the nanopillars (1305) were fully touching as shown in FIG. 13B. By measuring a beam current and exposure time, the Applicants determined that by using a dose of approximately 10,000 mC/cm2 full contraction of the nanopillars (1305) can be achieved as shown in FIG. 13B. This dose matches other results corresponding to a full cross-linking of PMMA (see, for example, reference 27). As can be seen in FIG. 13C the nanopillars (1305) are back to their original position after PMMA removal. With reference to FIG. 13B, a consequence of exposing a resist such as PMMA is its resilience to dissolution by acetone (see, for example, references 26-27). Once an area of interest was exposed a sample comprising the ring (1300) was dipped in acetone to remove a non-exposed portion of the PMMA, leaving the nanopillars (1305) locked in place while freeing the rest of the sample from the PMMA. This permits further possible processing to be performed on the sample. According to various embodiments of the present disclosure, pillars can be relaxed from deformation by heating, causing the PMMA to reflow or by removing the PMMA using an oxygen plasma. FIG. 13C shows the ring (1300) after applying oxygen plasma.

As will be described in below, in order to estimate a strain induced in pillars, a structure was analyzed by the Applicants in a manner similar to Timoshenko's treatment of a bimetallic strip (see, for example, reference 28). The actual geometry and material characteristics of a cross-linked region are difficult to measure and likely nonuniform, in reality behaving as a distributed film rather than an isolated region with clear boundaries. Additionally, the system could be complicated by slip at the interface, nonlinear elastic behavior of the polymer, and increasingly surface-dominated mechanical characteristics at the nanoscale. In spite of the simplified model, however, the proposed treatment shows excellent agreement with experimental data. Furthermore, the analysis predicts a constant radius-of-curvature yielding a conservative estimate of the maximum strain.

Figure 14B:
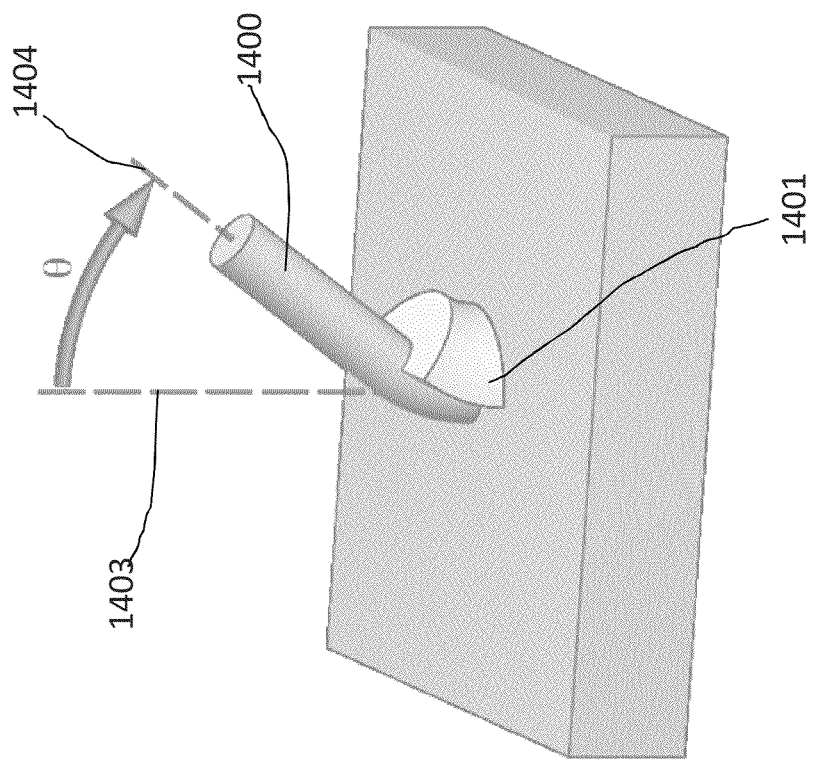
FIGS. 14A-B show diagrams of a theoretical model used to analyze pillar deformation.
Figure 14A:
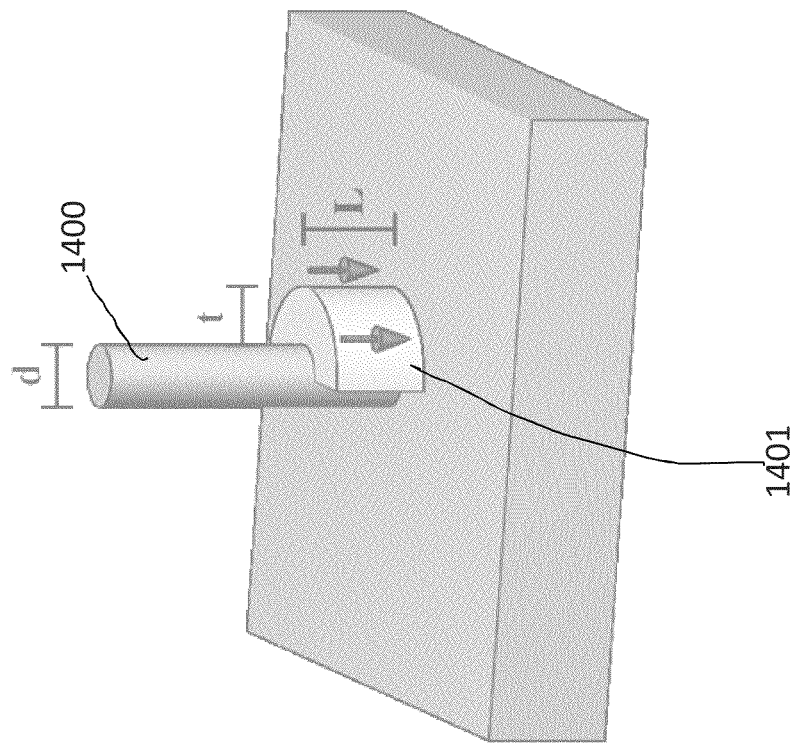

As shown in FIG. 14A, the Applicants modeled a pillar (1400) as a cylinder with diameter d, and approximated a cross-linked region (1401) of PMMA which contributes to the deformation as a semicircular shell around the pillar (1400) with radial thickness t and originally spun to a film thickness L. After exposure, the cross-linked region (1401) would undergo a uniform vertical contraction (as shown in FIG. 14B) by an amount ΔL (not shown), corresponding to a unit contraction $$\alpha = \frac{\Delta L}{L}.$$

This causes the pillar (1400) to bend to an exit angle θ between a pillar axis (1404) and substrate normal (1403).

Following Timoshenko, one can find:

$$\frac{1}{\rho} = \frac{\alpha(C_p - C_s)}{\frac{I_s}{A_s} + \frac{I_p}{A_p} + + \frac{E_s I_s}{E_p A_p} + \frac{E_p I_p}{E_s A_s} + (C_p - C_s)^2} \qquad (1)$$

where ρ is the radius of curvature and $$\alpha = \frac{\Delta L}{L}$$

is the unit contraction of the PMMA. Cp, Cs denote the center-of-mass coordinates, Ip, Is the cross-sectional moments, Ap, As the areas, and Ep, Es the Young's moduli for the PMMA and silicon, respectively. The exit angle θ=L/ρ can be obtained as follows:

$$\theta = \frac{L\alpha(C_p - C_s)}{\frac{I_s}{A_s} + \frac{I_p}{A_p} + + \frac{E_s I_s}{E_p A_p} + \frac{E_p I_p}{E_s A_s} + (C_p - C_s)^2} \qquad (2)$$

Referring to FIG. 14, for the geometry described above and assuming a coordinate system where x=0 corresponds to a center of the pillar (1400), the following equations can be obtained:

$$C_s = 0$$

$$C_p = \frac{3d^2 + 6dt + 4t^2}{3\pi(d + t)}$$

$$A_s = \frac{\pi d^2}{4}$$

$$A_s = \frac{\pi(d + 1)}{2}$$

$$I_s = \frac{\pi d^4}{64}$$

$$I_p = A_p \left( \frac{d^2 + 2dt + 2t^2}{8} - C_p^2 \right)$$

Taking Es=160 GPa and Ep~5 GPa as the Young's modulus for the exposed PMMA (see, for example, reference 27), one can solve for the remaining free parameters using a least-squares fit between the measured pillar angles and the analytic expression for θ, obtaining ΔL~43 nm and t~46 nm. This contraction is on the order of the vertical contraction in overexposed PMMA reported elsewhere (see, for example, reference 27).

Figure 15A:
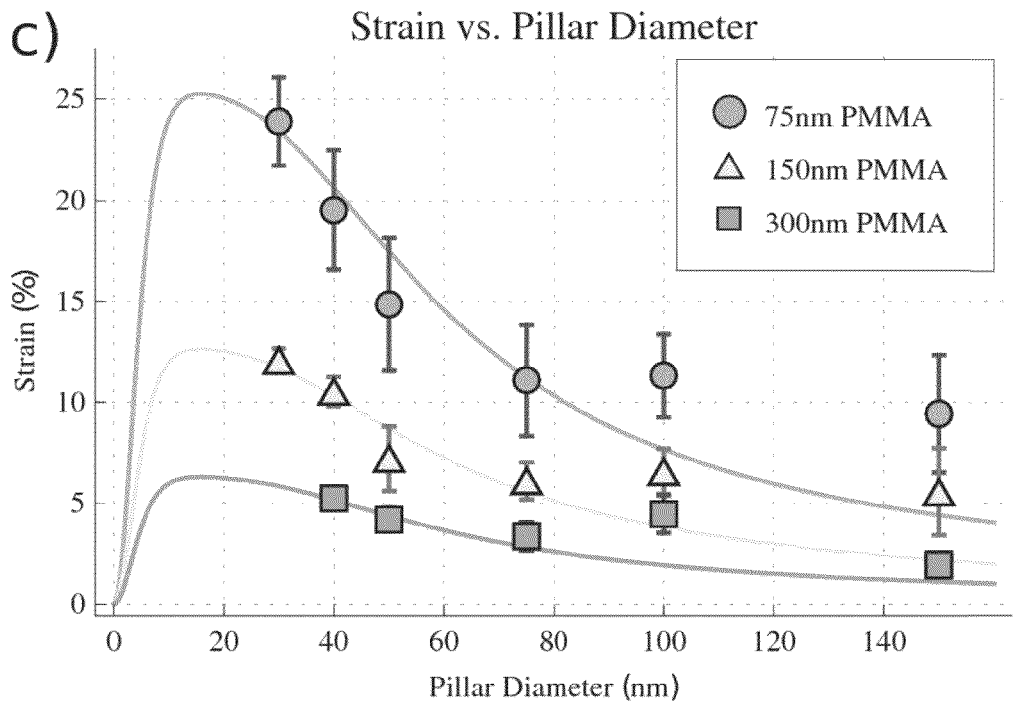
FIG. 15A-B show plots of bend angle and strain vs. pillar diameter respectively.
Figure 15B:
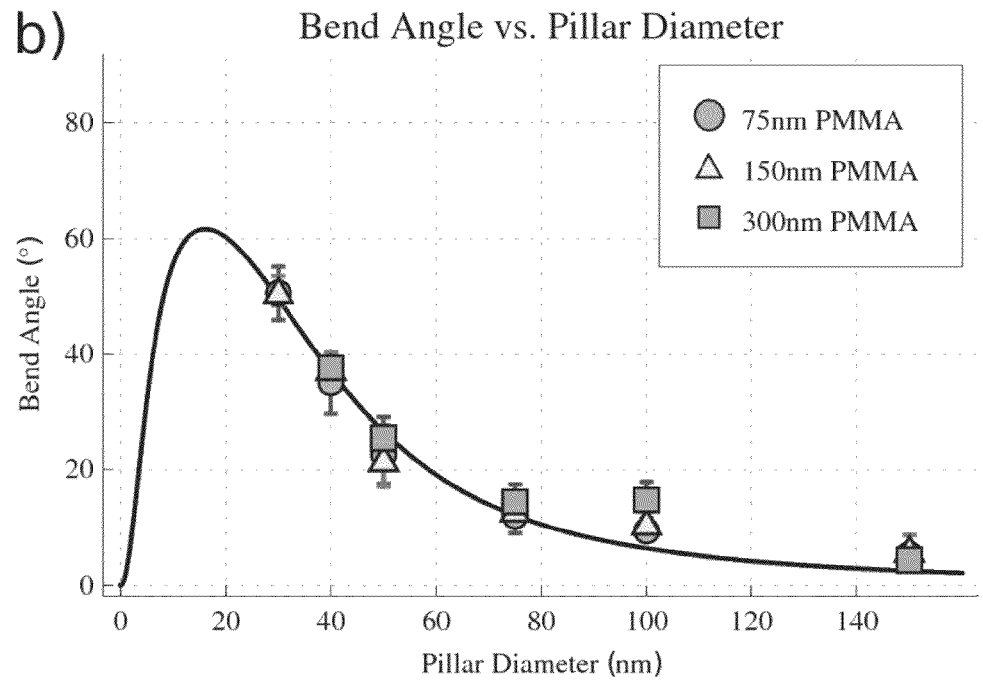

Some results related to the above-described analysis are shown in FIGS. 15A-B. FIG. 15A shows a plot of the exit angle θ of FIG. 14 vs. the Pillar diameter d as shown in FIG. 14. As can be seen in FIG. 15A, the exit angle θ does not show any measurable dependence on resist thickness. Referring to the equations described above, this corresponds to a fixed ΔL rather than a fixed unit contraction α as one might expect. The cause of this behavior might indicate that the deformation is occurring over a length which is smaller than the total resist thickness. If this is the case, the strain required to accomplish the same deformation over a reduced distance would be higher than that estimated. Were this distance also fixed, the strain curves would be independent of the PMMA starting thickness.

With further reference to FIG. 14, in order to provide a conservative strain estimate, it is assumed that the deformation is uniform and occurs over the entire submerged length of the pillar. It is noted that the portion of the pillar which extends beyond the PMMA remains unstrained. Using $$\varepsilon = \frac{\Delta \rho}{\rho}$$

for the strain, a maximum strain can be found as:

$$\varepsilon = \frac{\Delta L \alpha (C_p - C_s)(C_n - C_e)}{L\left(\frac{I_s}{A_s} + \frac{I_p}{A_p} + \frac{E_s I_s}{E_p A_p} + \frac{E_p I_p}{E_s A_s} + (C_p - C_s)^2\right)} \quad (3)$$

where Δρ=Cn−Ce is the distance between a neutral axis (Cn) and a far edge of the pillar (1400) i.e., Ce:

$$C_n = \frac{E_s A_s C_s + E_p A_p C_p}{E_s A_s + E_p A_p}$$

$$C_e = -\frac{d}{2}$$

Related results are plotted in FIG. 15B. Throughout the present disclosure, the term 'neutral axis' refers to a location in a bent pillar where there is no strain. As shown in FIG. 15B, the Applicants could controllably incorporate a 23.9% strain in 30 nm diameter single crystal nanopillars. Throughout the present disclosure, the term 'strain' is defined as the ratio between the amount of elongation or compression of the pillar to the length of the original pillar. The strain profile within the pillar is anisotropic. Based on the location of the neutral axis, it is possible to introduce both tensile and compressive strain or solely tensile. For large pillar diameters, the neutral axis lies inside the pillar, resulting in tensile strain at an outer edge and compressive strain on an inner edge. As the diameter decreases, however, the neutral axis moves toward the PMMA. For Cn>d/2, corresponding to d≤17.6 nm, the strain is tensile throughout the pillar cross section.

In what follows, the ability, methods for capturing small-scale size objects are described in accordance with an embodiment of the present disclosure. Throughout the present disclosure, the term 'small-scale size objects' intends to indicate objects with dimensions within nm to μm range.

Figure 16A:
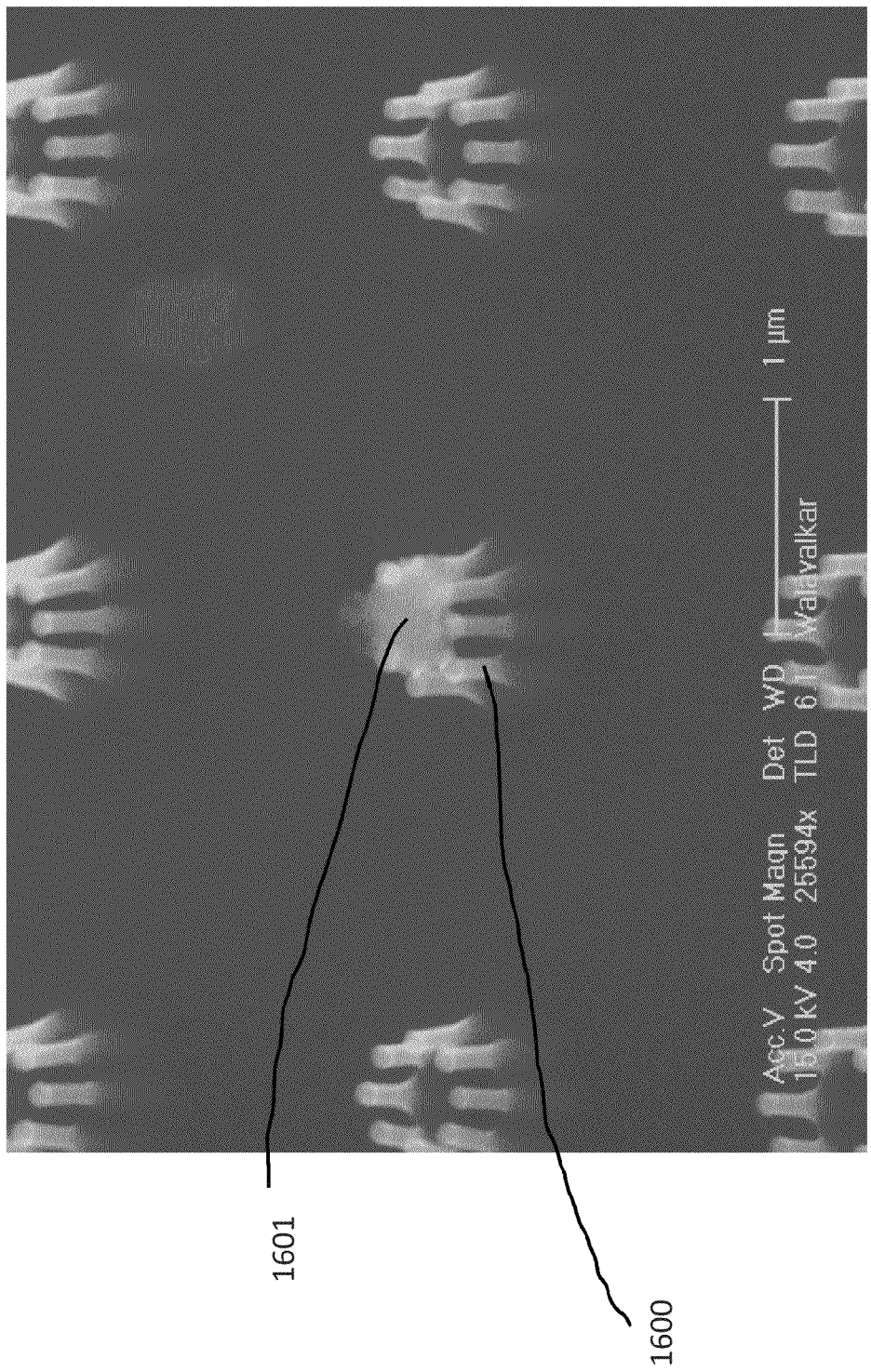
FIG. 16A shows a 300 nm alumina polishing bead captured by 100 nm pillars.
Figure 16B:
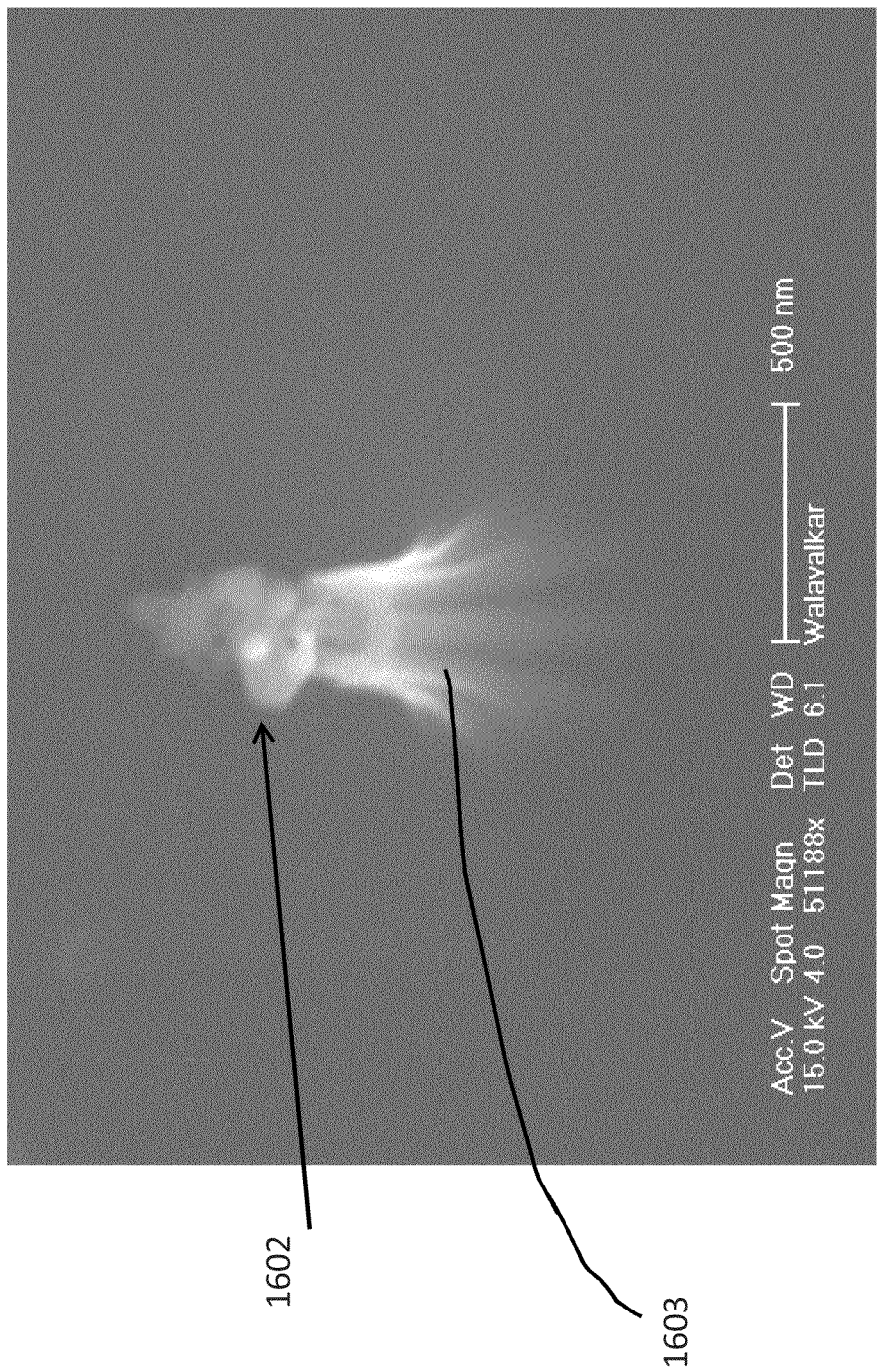
FIG. 16B shows 75 nm pillars capturing a collection of alumina beads.

FIG. 16A shows an array of pillars (1600) that had been selectively deformed using the methods described with reference to FIGS. 11-13 to capture a 300 nm aluminum oxide polishing bead (1601). FIG. 16B shows 75 nm pillars (1603) capturing a collection of alumina polishing beads (1602) with diameters within a range of 50 nm to 300 nm. During capture, a contraction of the array of pillars (1603) squeezed the beads (1602) such that they were forced through top of the closed pillars (1603) as shown in FIG. 16B. Once the pillars (1603) had been closed, the resist was selectively removed and the captured collection of the beads (1602) remained trapped within the pillars (1603). The Applicants expect this technique to have biological applications such as capturing individual cells for further study.

All references cited throughout the present disclosure are incorporated herein by reference in their entirety.

The present disclosure has shown methods for fabrication of high aspect ratio probes and deforming high aspect ratio micropillars and nanopillars related fabrication processes. While the high aspect ratio probes and related fabrication processes and methods for deforming high aspect ratio micropillars and nanopillars have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

LIST OF REFERENCES

1. "Comparison of the device physics principles of p-n junction nanorod solar cells," B. M. Kayes, H. A. Atwater, N. S. Lewis, J. Appl. Phys, 97, 114302, (2005).
2. "High-Performance Fully Depleted Silicon Nanowire (Diameter ≤5 nm) Gate-All-Around CMOS Devices" N. Singh, A. Agarwal, L. K. Bera, T. Y. Liow, R. Yang, R. C. Rustagi, C. H. Tung, R. Kumar, G. Q. Lo, N. Balasubramanian, D. L. Kwong, IEEE. Electron Device Lett, 27, 383-386 (2006).
3. "Rapid Fabrication of High Aspect Ratio Silicon. Nanopillars for Chemical Analysis" L. Sainiemi, H. Keskinen, M. Aromaa, L. Luosujarvi, K. Grigoras, T. Kotiaho, J. M. Makela, S. Franssila, 18, 505303, (2007).
4. "Strength and fracture of Si micro-pillars: A new SEM-based micro-compression test" B. Moser, K. Wasmer, L. Barbieri, J. Michler, J. Mater. Res., 22, 1004-1011, (2007).
5. R. N. Sajjad, K. Alam, J. Appl. Phys., 105, 044307, (2009).
6. "Single-nanowire Si solar cells," M. D. Kelzenberg, D. B. Turner-Evans, B. M. Kayes, M. A. Filler, M. C. Putnam, N. S. Lewis, H. A. Atwater, Nano Lett, 8, 710-714, (2008).
7. "Self-masked high-aspect ration polymer nanopillars" Y. F. Chang, Q. R. Chou, J. Y. Lin, C. H. Lee, Appl. Phys. A., 86, 193-196, (2007).
8. "Critical tasks in high aspect ratio silicon dry etching for microelectromechanical systems" I. W. Rangelow, J. Vac. Sci. Technol. A, 21, 1550-1562, (2003).
9. "Guidelines for etching silicon MEMS structures using lasmas at cryogenic temperatures" M. J. deBoer, J. G. E. Gardeniers, H. V. Jansen, E. Smulders, M J. Gilde, G. Roelofs, J. N. Sasserath, M. Elwenspoek, J. Microelectromech. Syst. 1, 385 (2002).

10. "Silicon etch process options for micro- and nanotechnology using inductively coupled plasmas" C. C. Welch, A. L. Goodyear, T. Wahlbrink, M. C. Lemme, T. Mollenhauer, Microelectron. Eng. 83, 1170-1173, (2006).
11. "Mask Material Effects in. Cryogenic Deep Reactive Ion Etching" L. Sainiemi, S. Franssila, J. Vac. Sci. Technol. B, 25, 801-807, (2007).
12. "Etch rates for micromachining processing part" K. R. Williams, K. Gupta, M. Wasilik, J. Microelectromech. Syst., 12, 761-778, (2003).
13. "Maximum Achievable Aspect Ratio in Deep Reactive Ion Etching of Silicon due to Aspect Ratio Dependent Transport and the Microloading Effect," J. Yeom, Y. Wu, J. C. Selby, M. A. Shannon, J. Vac. Sci. Technol. B, 23, 2319-2329, (2005).
14. Oxford Plama Technology Applications Engineering Group "Plasmalab" Process Data Sheet, 'Bosch' Silicon Etch Process, 'Cryo' Silicon Etch Process, and Silicon Etch Process.
15. "Silicon nanopillars for mechanical single-electron transport," Scheible, D.; Blick, R. Appl. Phys. Lett. 84, 4632, (2004).
16. "Field emission from a single nanomechanical pillar" Kim, H.; Qin, M., H. and Westphall; Smith, L.; Blick, R. Nanotechnology 18, 4, (2007).
17. "Epitaxial core-shell and core-multishell nanowire heterostructures,", Lauhon, L.; Gudiksen, M.; Wang, D.; Lieber, C. Nature, 420, 57, (2002).
18. "Electroluminescent device based on silicon nanopillars", Nassiopoulos, A.; Grigoropoulos, S.; Papadimitriou, D. Appl. Phys. Lett., 69, 2267, (1996).
19. "Photoluminescence from nanocrysstaline silicon in Si/SiO2 superlattices" Photopoulos, P.; Nassiopoulou, A.; Kouvatsos, D.; Travlos, A. Appl. Phys. Lett., 76, 3588, (2000).
20. "Fabrication and actuation of customized nanotweezers with a 25 nm gap" Boggild, P.; Hansen, T.; Tanasa, C.; Grey, F. Nanotechnology 12, 331, (2001).
21. "Finite temperature quasicontinuum method for multiscale anaylysis of silicon nanostructures" Tang, Z.; Xu, Y.; Li, G.; Aluru, N. J. Appl. Phys., 97, 114304, (2005).
22. "Electronic and optoelectronic properties of semiconductor structures" Singh, J. In Electronic and optoelectronic properties of semiconductor structures; Cambridge University Press,; Chapter 1.4 Strained heterostructures, pp 26-31, (2003).
23. "Asymmetric strain in nano-scale patterned strained-Si/strained-Ge/strained-Si heterostructures on insulator, "", Hashemi, P.; Gomez, L.; Hoyt, J.; Robertson, M.; Canonico, M. Appl. Phys. Lett., 91, 083109, (2007).
24. "Strained silicon as a new electro-optic material," Jacobsen, R.; Andersen, K.; Borel, P.; Pedersen, J.; Frandsen, L.; Hansen, O.; Kristensen, M.; Lavirnenko, A.; Moulin, G.; Ou, H.; Peucheret, C.; Zsigri, B.; Bjarkalev, A. Nature 44, 199, (2006).
25. "Periodically poled silicon,", Hon, N.; Tsia, K.; Solli, D.; Jalali, B. Appl. Phys. Lett., 94, 091116, (2009).
26. "Crosslinked PMMA as a high-resolution negative resist for electron beam lithography and applications for physics of lowdimensional structures" Zailer, I.; Frost, J.; Chabasseur-Molyneux, V.; Ford, C.; Pepper, M. Semicond. Sci. Technol, 11, 1235. 12, (1996).
27. "Cross-linked PMMA as a low dimensional sacrifcial layer", Teh, W. H.; Liang, C.-T.; Graham, M.; Smith, C. G. Journal of Microelectromechanical Systems, 12, 641-648, (2003).
28. "Analysis of Bi-metal thermostats," Timoshenko, S. J. Opt. Soc. Am., 11, 233-256, (1925).

The invention claimed is:
1. A method for fabricating an array of high aspect ratio probes comprising:
providing a substrate;
coating the substrate with a first resist;
defining high aspect ratio nanopillars by lithographically patterning the first resist, thus forming a patterned first resist;
developing, with a developer, the patterned first resist to remove portions of the first resist on the substrate, thus forming a developed first resist and exposing portions of the substrate;
depositing an etch mask on the developed first resist and the exposed portions of the substrate to mask the exposed portions of the substrate;
coating the deposited etch mask with a second resist different from the first resist;
defining a placement of high aspect ratio micropillars by lithographically patterning the second resist, thus forming a patterned second resist;
developing, with a developer, the patterned second resist to remove portions of the second resist on an underlying layer comprising the deposited etch mask on both the developed first resist and the exposed portions of the substrate, thus exposing portions of the underlying layer;
performing a first etch with an SF6/O2 cryogenic etch to etch away unmasked portions of the substrate, thus creating the high aspect ratio micropillars in the underlying layer;
removing, by way of chemical reactions, the developed second resist;
placing the substrate in a chemical bath to dissolve, by way of chemical reactions, the developed first resist and the deposited etch mask on the developed first resist such that the deposited etch mask on the substrate remains undissolved;
performing a second etch with a SF6/C4F8 etch, thus establishing the high aspect ratio nanopillars;
removing a remainder of the deposited etch mask, thus forming the high aspect ratio nanopillars on the high aspect ratio micropillars; and
recoating the substrate with a third resist and selectively removing the third resist to define an exposed portion and a third resist covered portion of the substrate, the exposed portion including at least top regions of the high aspect ratio nanopillars and adapted to define a metal pattern;
depositing a metal layer on both the exposed portion and the third resist covered portion of the substrate; and
lifting off the third resist and the metal layer that is on the third resist covered portion of the substrate, thus leaving behind portions of the metal layer on the exposed portion of the substrate corresponding to the high aspect ratio nanopillars, thus creating metal contacts for the high aspect ratio nanopillars and thereby generating the array of high aspect ratio probes.
2. A method for fabricating an array of high aspect ratio probes comprising:
providing a substrate;
coating the substrate with a first resist;
defining high aspect ratio nanopillars by lithographically patterning the first resist, thus forming a patterned first resist;

developing, with a developer, the patterned first resist to remove portions of the first resist on the substrate, thus forming a developed first resist and exposing portions of the substrate;

depositing an etch mask on the developed first resist and the exposed portions of the substrate to mask the exposed portions of the substrate;

coating the deposited etch mask with a second resist different from the first resist;

defining a placement of high aspect ratio micropillars by lithographically patterning the second resist, thus forming a patterned second resist;

developing, with a developer, the patterned second resist to remove portions of the second resist on an underlying layer comprising the deposited etch mask on both the developed first resist and the exposed portions of the substrate, thus exposing portions of the underlying layer;

performing a first etch with an SF6/O2 cryogenic etch to etch away unmasked portions of the substate, thus creating the high aspect ratio micropillars in the underlying layer;

removing, by way of chemical reactions, the developed second resist;

placing the substrate in a chemical bath to dissolve, by way of chemical reactions, the developed first resist and the deposited etch mask on the developed first resist such that the deposited etch mask on the substrate remains undissolved;

performing a second etch with an SF6/C4F8 etch, thus establishing the high aspect ratio nanopillars;

removing a remainder of the deposited etch mask, thus forming the high aspect ratio nanopillars on the high aspect ratio micropillars; and recoating the substrate with a third resist and selectively removing the third resist to define an exposed portion and a third resist covered portion of the substrate, the exposed portion including at least top regions of the high aspect ratio nanopillars and adapted to define a metal pattern;

depositing a metal layer on both the exposed portion and the third resist covered portion of the substrate; and lifting off the third resist and the metal layer that is on the third resist covered portion of the substrate, thus leaving behind portions of the metal layer on the exposed portion of the substrate corresponding to the high aspect ratio nanopillars, thus creating metal contacts for the high aspect ratio nanopillars and thereby generating the array of high aspect ratio probes, wherein the first resist is an electron-beam resist, the second resist is a photoresist and the etch mask is an alumina etch mask.

3. A method for fabricating an array of high aspect ratio probes comprising:
providing a substrate;
coating the substrate with a first resist;

defining high aspect ratio nanopillars by lithographically patterning the first resist, thus forming a patterned first resist;

developing, with a developer, the patterned first resist to remove portions of the first resist on the substrate, thus forming a developed first resist and exposing portions of the substrate;

depositing an etch mask on the developed first resist and the exposed portions of the to mask the exposed portions of the substrate;

coating the deposited etch mask with a second resist different from the first resist;

defining a placement of high aspect ratio micropillars by lithographically patterning the second resist, thus forming a patterned second resist;

developing, with a developer, the patterned second resist to remove portions of the second resist on an underlying layer comprising the deposited etch mask on both the developed first resist and the exposed portions of the substrate, thus exposing portions of the underlying layer;

performing a first etch with an SF6/O2 cryogenic etch to etch away unmasked portions of the substate, thus creating the high aspect ratio micropillars in the underlying layer;

removing, by way of chemical reactions, the developed second resist;

placing the substrate in a chemical bath to dissolve, by way of chemical reactions, the developed first resist and the deposited etch mask on the developed first resist such that the deposited etch mask on the substrate remains undissolved;

performing a second etch with an SF6/C4F8 etch, thus establishing the high aspect ratio nanopillars;

removing a remainder of the deposited etch mask, thus forming the high aspect ratio nanopillars on the high aspect ratio micropillars; and recoating the substrate with a third resist and selectively removing the third resist to define an exposed portion and a third resist covered portion of the substrate, the exposed portion including at least top regions of the high aspect ratio nanopillars and adapted to define a metal pattern;

depositing a metal layer on both the exposed portion and the third resist covered portion of the substrate; and lifting off the third resist and the metal layer that is on the third resist covered portion of the substrate, thus leaving behind portions of the metal layer on the exposed portion of the substrate corresponding to the high aspect ratio nanopillars, thus creating metal contacts for the high aspect ratio nanopillars and thereby generating the array of high aspect ratio probes, wherein the high aspect ratio nanopillars have diameters ranging from 30 to 50 nm with aspect ratios greater than 25 and the nanopillars are controllably placed within a distance of 50 nm or more from one another.

\* \* \* \* \*